(12) United States Patent
Devanaboyina

(10) Patent No.: US 9,474,482 B2
(45) Date of Patent: Oct. 25, 2016

(54) METHOD FOR DIAGNOSIS AND TREATMENT OF DISORDERS OF THE GASTROINTESTINAL TRACT, AND APPARATUS FOR USE THEREWITH

(75) Inventor: Udaya Sankar Devanaboyina, Fremont, CA (US)

(73) Assignee: G-Tech Medical, Inc., Mountain View, CA (US)

(*) Notice: Subject to any disclaimer, the term of this patent is extended or adjusted under 35 U.S.C. 154(b) by 956 days.

(21) Appl. No.: 13/373,042

(22) Filed: Nov. 1, 2011

(65) Prior Publication Data

US 2013/0046150 A1 Feb. 21, 2013

Related U.S. Application Data

(60) Provisional application No. 61/409,038, filed on Nov. 1, 2010.

(51) Int. Cl.
*A61B 5/00* (2006.01)
*G06F 19/00* (2011.01)
*A61B 5/0402* (2006.01)
(Continued)

(52) U.S. Cl.
CPC ............... *A61B 5/42* (2013.01); *G06F 19/34* (2013.01); *G06F 19/345* (2013.01); *G06F 19/3418* (2013.01); *A61B 5/0024* (2013.01); *A61B 5/0402* (2013.01); *A61B 5/0476* (2013.01); *A61B 5/04884* (2013.01); *A61B 5/08* (2013.01); *A61B 5/11* (2013.01); *A61B 5/6823* (2013.01); *A61B 5/6831* (2013.01)

(58) Field of Classification Search
CPC A61B 5/04; A61B 5/04012; A61B 5/04884; A61B 5/0492; A61B 5/227; A61B 5/42; A61B 5/4238; A61B 5/6813; A61B 5/4255
See application file for complete search history.

(56) References Cited

U.S. PATENT DOCUMENTS 5,704,368 A * 1/1998 Asano et al. .................. 600/382
5,857,980 A * 1/1999 Wilson .......................... 600/546
(Continued)

FOREIGN PATENT DOCUMENTS

WO WO 9610358 A1 * 4/1996
WO 2010/068818 6/2010
(Continued)

OTHER PUBLICATIONS

Haddab, S. et al "Microcontroller-Based System for Electrogastrography Monitoring Through Wireless Transmission"; Measurement Science Review, vol. 9, No. 5, 2009, p. 122-126.*
(Continued)

*Primary Examiner* — William Thomson
*Assistant Examiner* — Marie Archer
(74) *Attorney, Agent, or Firm* — Aurora Counsulting LLC

(57) ABSTRACT

A method for diagnosing motility disorders of a gastrointestinal tract of a body. The method can include measuring electrical signals from the gastrointestinal tract while the patient is engaged in normal daily activities, recording the measured electrical signals on a portable electronic device carried by the body, recording by the patient in real time one or more symptoms of the body and analyzing characteristics of the recorded electrical signals with the recorded symptoms of the body to diagnosis gastrointestinal disorders of the body. Apparatus for use therewith and methods for treatment thereof are provided.

12 Claims, 21 Drawing Sheets

(51) Int. Cl.
*A61B 5/0476* (2006.01)
*A61B 5/0488* (2006.01)
*A61B 5/08* (2006.01)
*A61B 5/11* (2006.01)

(56) References Cited

U.S. PATENT DOCUMENTS

| | | | |
|---|---|---|---|
| 7,160,254 B2* | 1/2007 | Noar | 600/538 |
| 2003/0069714 A1 | 4/2003 | Wigley et al. | |
| 2004/0260164 A1 | 12/2004 | Kilcoyne et al. | |
| 2005/0209709 A1 | 9/2005 | Bradshaw | |
| 2005/0215917 A1* | 9/2005 | Noar | A61B 5/04884 600/546 |
| 2006/0058606 A1 | 3/2006 | Davis et al. | |
| 2006/0107954 A1 | 5/2006 | Katz et al. | |
| 2006/0149541 A1 | 7/2006 | Jaklitsch et al. | |
| 2006/0258927 A1 | 11/2006 | Edgar, Jr. et al. | |
| 2007/0225576 A1 | 9/2007 | Brown et al. | |
| 2007/0287931 A1 | 12/2007 | Dilorenz | |
| 2008/0154110 A1* | 6/2008 | Burnes et al. | 600/382 |
| 2009/0318783 A1 | 12/2009 | Rohde et al. | |
| 2010/0172839 A1 | 7/2010 | Walker | |
| 2010/0228105 A1 | 9/2010 | Policker et al. | |
| 2010/0292606 A1 | 11/2010 | Prakash et al. | |
| 2014/0226158 A1 | 8/2014 | Trainer | |

FOREIGN PATENT DOCUMENTS

| | | |
|---|---|---|
| WO | WO 2010121038 A1 * | 10/2010 |
| WO | 2012/060874 | 5/2012 |

OTHER PUBLICATIONS

Chen, JDZ et al; "Detection of gastric slow wave propagation from the cutaneous electogastrogram"; Am. J. Physiol. 277 (Gastrointest. Liver Physiol. 40): G424-G430, 1999.*

Kim, D, W; et al."Usefulness of a Developed Four-Channel EGG System with running spectrum analysis"; Yonsei Medici Journal; vol. 41; No. 2; 2000; 230-236.*

Garcia-Casado, J. et al; "Noninvasive Measurement and Analysis of Intestinal Myoelectrical Activity Using Surface Electrodes" IEEE Transactions on Biomedical Engineering, vol. 52, No. 6, Jun. 2005; p. 983-991.*

Chen, J.D. Z. et al; "Measurement of Electrical Activity of the Human Small Intestine Using Surface Electrodes"; IEEE Transactions on Biomedical Engineering, vol. 40, No. 6, Jun. 1993; p. 598-602.*

Lammers, W. J. E. P et al; "Origin and propagation of the slow wave in the canine stomach: the outlines of a gastric conduction system" Am J Physiol Gastrointest Liver Physiol 296: G1200-G1210, 2009.*

Leahy, A. et al; "Abnormalities of the Electrogastrogram in Functional Gastrointestinal Disorders"; American Journal of Gastroenteology; vol. 94, No. 4, 1999; pp. 1023-1028.*

Myers, T. J. et al; "Human Surface Electrogastrograms: AC and DC measurements"; Annals of Biomedical Engineering, vol. 12, pp. 319-333, 1984.*

Wang, Z. S. eta l; "Detection of gastric slow wave uncoupling from multi-channel electrogastrogram: validations and applications"; Neurogastroenterol Motil (2003) 15, 457-465.*

Sanders, K. M et al "Interstitial cells of Cajal as pacemakers in the gastrointestinal tract"; Annu. Rev. Physiol. 2006. 68:307-343.*

Written Opinion issued on PCT Application Serial No. PCT/US2011/01848 by ISA/US dated May 21, 2012, pp. 1-5.

International Search Report issued on PCT Application Serial No. PCT/US2011/01848 by ISA/US dated May 21, 2012, pp. 1-4.

International Search Report and Written Opinion issued for PCT/US2015/056282 by ISA/US dated Jan. 20, 2016 (9 pages).

* cited by examiner

Front View
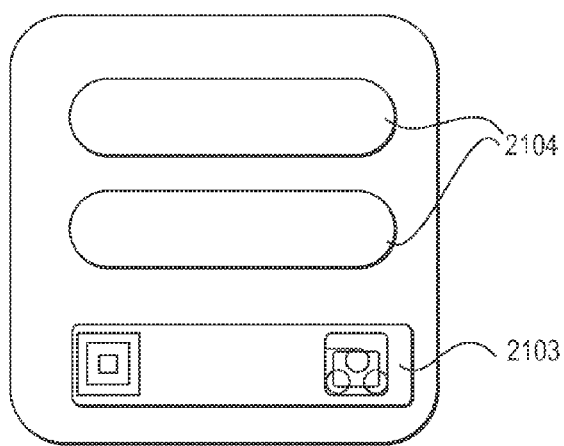
Side View
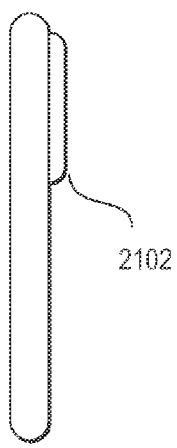
FIG. 21

METHOD FOR DIAGNOSIS AND TREATMENT OF DISORDERS OF THE GASTROINTESTINAL TRACT, AND APPARATUS FOR USE THEREWITH

RELATED APPLICATION

This application claims priority to U.S. provisional application Ser. No. 61/409,038 filed Nov. 1, 2010, the entire contents of which are incorporated herein by this reference.

FIELD OF TECHNOLOGY

This disclosure relates generally to the diagnosis and treatment of disorders of the gastrointestinal tract, and more particularly to the diagnosis and treatment of disorders of the lower gastrointestinal tract.

BACKGROUND

Functional disorders of the gastrointestinal tract and of the urinary bladder which include irritable bowel syndrome, constipation, gastroparesis, urinary and fecal incontinence affect a large number of people. These disorders are sometimes associated with abnormal contractility and motility of the affected organ. Various disorders of the gastrointestinal tract including tumors, ulcerative colitis, diverticulitis that result in organic changes are sometimes diagnosed using endoscopy, imaging, analysis of serum samples for biomarkers and by biopsy examination. However, functional disorders of the gastrointestinal tract such as irritable bowel syndrome are mostly diagnosed based on symptoms and most importantly, based on exclusion of organic diseases. Confirmatory tests like scintigraphy and manometry can be useful tools for such purposes.

In addition to the dysfunction of the primary organs, the gastrointestinal tract and urinary bladder, functional disorders are also associated with disorders of other organ systems. For example, gastroparesis can occur in a significant number of diabetes patients due to peripheral neuropathy. Similarly, psychological abnormalities and susceptibility to stress has been reported to be associated with the development of irritable bowel syndrome, constipation and hyperactivity of the bladder such as urinary incontinence.

Very limited diagnostic and treatment options that can provide an easy diagnosis and long term relief are available at present for people with functional disorders. As a result, the cost of diagnosing and treating functional disorders can be significant. There is a need for an integrative approach to diagnose and treat various functional disorders of the gastrointestinal tract.

BRIEF DESCRIPTION OF THE DRAWINGS

Example embodiments are illustrated without any limitation in the figures of the accompanying drawings, in which like references indicate similar elements and in which:

FIG. 21 is a schematic illustration of another embodiment of a sensor of the present invention.

Other features of the present embodiments will be apparent from the accompanying drawings and from the detailed description that follows.

DETAILED DESCRIPTION

The invention discloses systems, devices, apparatus and methods for acquiring physiological parameters from various organ systems for the purposes of monitoring, diagnosing, preventing or treating various disorders of a gastrointestinal tract in humans and animals. Although most of the discussion is focused on the gastrointestinal tract, it should be understood that the described invention can be used for diagnosis and management of disorders of other organ systems. The clinician may use the acquired data alone or in conjunction with patient symptoms and results from other diagnostic tests to diagnose and manage various gastrointestinal conditions, while the individual user or caretaker may use the invention to manage the disease condition as appropriate. In addition to diagnosis, the invention may be used for biofeedback purposes.

The systems, devices and methods disclosed herein may be implemented in any configuration for acquiring and processing data for the purposes of diagnosis or treatment of various gastrointestinal conditions described in this application, and may be executed in a form of a machine-readable medium for use in a computer or other electronic system embodying a set of instructions. Other features will be apparent from the accompanying drawings and from the detailed description that follows.

Figure 1:
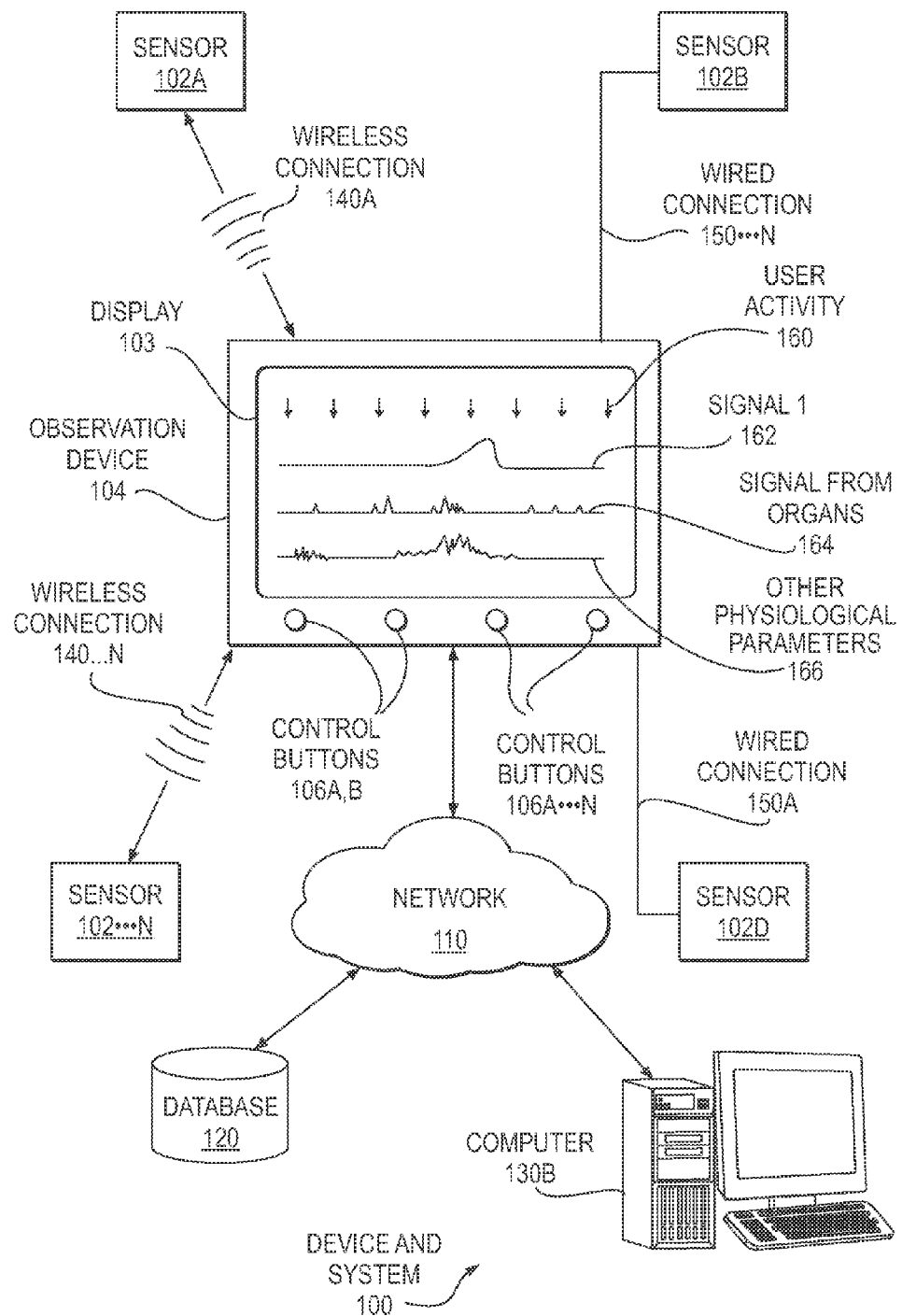
FIG. 1 is a view of a device and system 100 for diagnosis, treatment and training of gastrointestinal tract disorders in human and animals showing components and interfaces

FIG. 1 shows a device and a system 100 of the present invention that connects together an observation device 104, one or more sensors 102A . . . N, a network 110, a database 120 and computer readable media such as one or more computers 130A . . . N. The network 110 and the observation device 104 may be connected to each other via one or more wireless connections 140A . . . N or one or more wired connections 150 A . . . N. There may be multiple sensors or electrodes connected to the observation device 104 or the sensor 102 A . . . N may communicate data directly to the computer 130A . . . N. The observational device 104 may or may not contain a display unit 103. The data may be displayed either on the display module 103, on the computer 130A . . . N or both. The sensor may communicate with a network of computer readable media using a wire or a wireless protocol. The device may be used for sensing, recording, collecting, disseminating and storing various physiological parameters including, but not limited to electrical activity from various organs, for example the gastrointestinal tract, urinary bladder, brain and various muscle groups.

The observation device 104 may be any suitable portable electronic device such as a mobile communication device, a smart phone at tablet or a laptop computer. The device 104 may be of any suitable size and in one embodiment is sufficiently small so as to be capable of being carried by a human or other mammalian body. For example, the device 104 may be a hand held device.

The device 104 may contain one or more control buttons 106 A . . . N or touch or voice based means to record user inputs, for example symptoms of the body such as bowel movements, cramping, bloating, vomiting, nausea, heartburn, pain from chest, abdomen or pelvic regions, refluxing, incontinence, constipation, stool form, symptoms relating to gastrointestinal disorders including esophageal motility disorders, gastroparesis, gastroesophageal reflux disease, irritable bowel syndrome, constipation, incontinence and dyspepsia, symptoms relating to psychological disorders including stress, depression and anxiety. The same or other buttons 106 A . . . N or touch or voice based means may be used to record user inputs such as various events like eating, drinking, bowel movement, emesis, walking, jogging, traveling in a vehicle and sitting.

In addition, the same or other buttons 106 A . . . N or touch or voice based means may be used for selection of display parameters such as Signal 1, signal from organs 164, user activity 160 and other physiological parameters 166. These parameters may be displayed on display 103 or by any other suitable means on the device 104 and/or elsewhere. Examples of such parameters may include, but not limited to, electrical signals, skin conductivity, abdominal distention, respiratory activity, user movements, contractility, motility, intra-luminal and intra-abdominal pressure and sounds. Additional parameters such as electrical signals of other organs, for example the heart or the brain, respiration, movement and vibrations from external environment may be included. The acquired parameters together with events recorded automatically or manually by an individual or the patient may be used by clinicians for diagnosis and management of the disease condition.

In one embodiment, the system may consist solely of the observation device, which may be a cell phone, a smart phone, and hand held electronic device, a computer or a tablet type device, which can be connected to the sensors by any suitable means such wires or wireless transmitters and receivers. For example, portable device may be easily carried around by the individual to enable acquiring signals by the patient when the patient is in an ambulatory mode, for example engaging in normal daily activities or otherwise outside of a hospital or clinical setting.

In another embodiment, the observation device may communicate with other devices such as head gear, listening devices, vibration cancellation devices, mobile devices or network devices. The observation device may also communicate with a network that stores, retrieves and communicates wirelessly.

In another embodiment, the parameters collected and recorded by the device may be used for performing signal enhancement, signal conditioning, signal analysis, signal noise correction, pattern recording, pattern matching and pattern prediction for the purpose of monitoring, diagnosis and treatment.

In one embodiment, the system may include hardware, software and network devices that may be connected to each other. The software may contain various modules and be flexible to integrate new modules as needed. The system may also be wireless area networks, local area networks and be wireless ready. The system may include mobile devices, sensors, visual, tactile and auditory cancellation devices, computers and receiving devices, and any combination thereof.

In one embodiment, the software may be stored and implemented in any computer readable medium. The individual may be able to view, analyze, annotate, store and retrieve the data using a graphical individual interface on the observation device or any other device of the system.

In another embodiment, a system is enabled for analog to digital conversion, to convert analog physiological data of the individual into a digital physiological data for further processing.

In another embodiment, a system for enabling the communication between a physiological data collecting device and a health care monitoring center, so as to transmit physiological data of the individual to the appropriate health care provider and to further permit the health care monitoring center to send feedback and guidance to the individual through the observation device or any other device of the system.

The device may be combined with other devices or may be equipped with additional sensors that can record the gastrointestinal tract pH, motility, pressure, chemical composition of the gastrointestinal tract contents. The device may be used for recording the electrical activity of other organ systems including but not limited to cardiovascular, pulmonary, urinary, reproductive and musculoskeletal systems. The internally placed device may be able to communicate wirelessly through another device placed externally to record and store the data for further transmission, storage or analysis. For example, the observation device, or any other device of the system may be wireless or otherwise electrically coupled to one or more electrodes mounted on the skin of the patient in the vicinity of all or a portion of the gastrointestinal tract, one or more electrodes mounted on the head of the patient for measuring electrical signals by means of electroencephalography, one or more electrodes mounted on the skin of the patient in the vicinity of skeletal muscle groups in the body, for example in the abdominal and pelvic regions of the body, for measuring electrical signals by means of electromyography, one or more electrodes mounted on the skin of the body for measuring cardiac electrical signals by means of electrocardiography, one or more sensors mounted on the skin of the body for measuring skin conductance of the body, and/or one or more electrodes mounted on the skin of the body for measuring respiratory signals of the body. One or more internal electrodes can also be used for recording electrical signals from within the body for the foregoing purposes.

The database 120 may be used for storage of collected data, data analysis and retrieval of data for further use.

The device may be stationary or mobile and may be a part of a network. As an example, without any limitations, the device may be used in babies, young children and or older adults or in other age groups to detect when there is an electrical activity that is associated with bowel movement, so that the individual or caretaker can take appropriate action to relieve the bowels. An additional example is that the device may be used in all age groups, to make an individual ignore certain signals from the urinary bladder and surrounding region. Without any limitation, a stationary type device of the system for example may be more suitable for emergency rooms, hospitals, clinics, or physician's office while a portable device may be more useful for individual use outside of a hospital or clinical setting, although they can be interchangeable.

Figure 2:
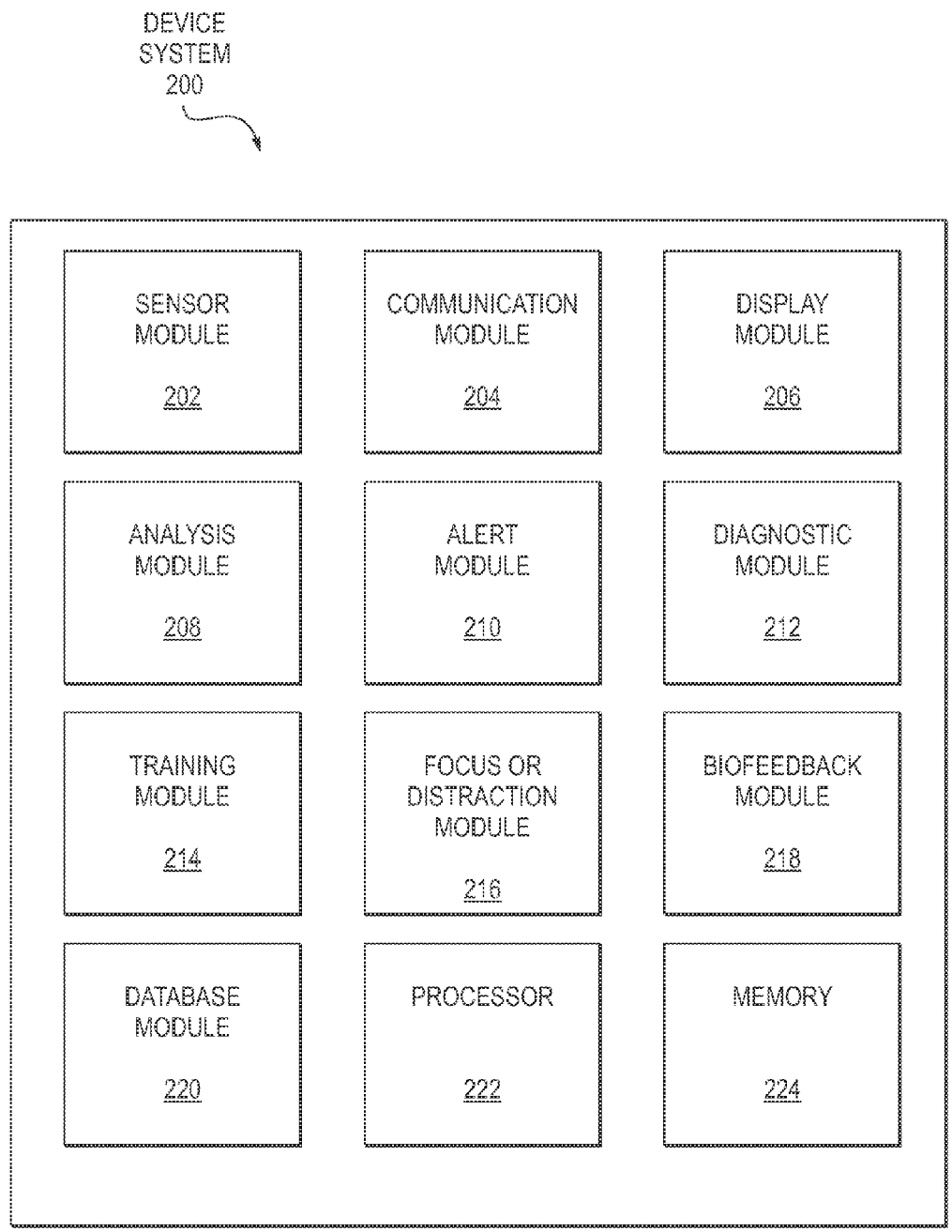
FIG. 2 illustrates a functional view of a system 200 with various modules including a processor and memory to run the software.

FIG. 2 is a schematic overview of one embodiment of a device and system 200 of the present invention. System 200 can have a use and function similar to system 100 described above or mobile device 104 described above. System 200 includes a memory 224 and a processor 222 to process various software modules such as sensor module 202, communication module 204, display module 206, analysis module 208, alert module 210, diagnostic module 212, training module 214, focus or sensor distraction module 216, biofeedback module 218 and a database module 220. For example, the sensor module 202 may be used for collecting signals 162, signals from organ 164, other physiological parameters 166 for display, diagnosis, data collection, training and storage. The sensor module 202 may be a standalone piece of software downloadable on a subscription basis or embedded in each sensor or may be up-loaded in one or more computers 130A . . . N for use by a care taker, a physician or the individual user or patient. Analysis module 208 allows the individual to analyze the data collected by sensor module 202 using an algorithm. The data collected by the sensors 102 A . . . N, such as electrical signals and characteristics of such signals, is analyzed using an appropriate software application and algorithms and is stored, displayed, transmitted and/or analyzed for use by the individual or care taker or healthcare provider. The device of the system 200 with the application, such as observation device 104, may be used for diagnosis or treatment purposes. Such device, such as observation device 104, may be a standalone device or combined with other devices of the system 200 that measure similar parameters. The display module 206 may enable the individual to view the real time analyzed data as it is being captured or previously recorded data. The diagnostic module 212 may use the input from analysis module 208 and help the individual to diagnose the condition and help suggest a treatment method. Parameter selection module 216 can allow the care taker or the physician or the individual to select the mode of diagnosis such as urinary incontinence or constipation mode. The alert module 210 based on the parameter selection module 216 can alert the individual or the individual or the physician about a particular status for diagnosis, treatment or a physical task such as defecation to be performed. The biofeedback module 218 can enable the individual to get alerted or trained to recognize the status and react accordingly. The database module 220 may be used for storing, recollecting and storing treatment method steps in the sensor, observation device or computer. The whole device and system 200 may be an integral part of the observation device 104 or all or parts thereof can be managed remotely through a network 110.

Figure 3:
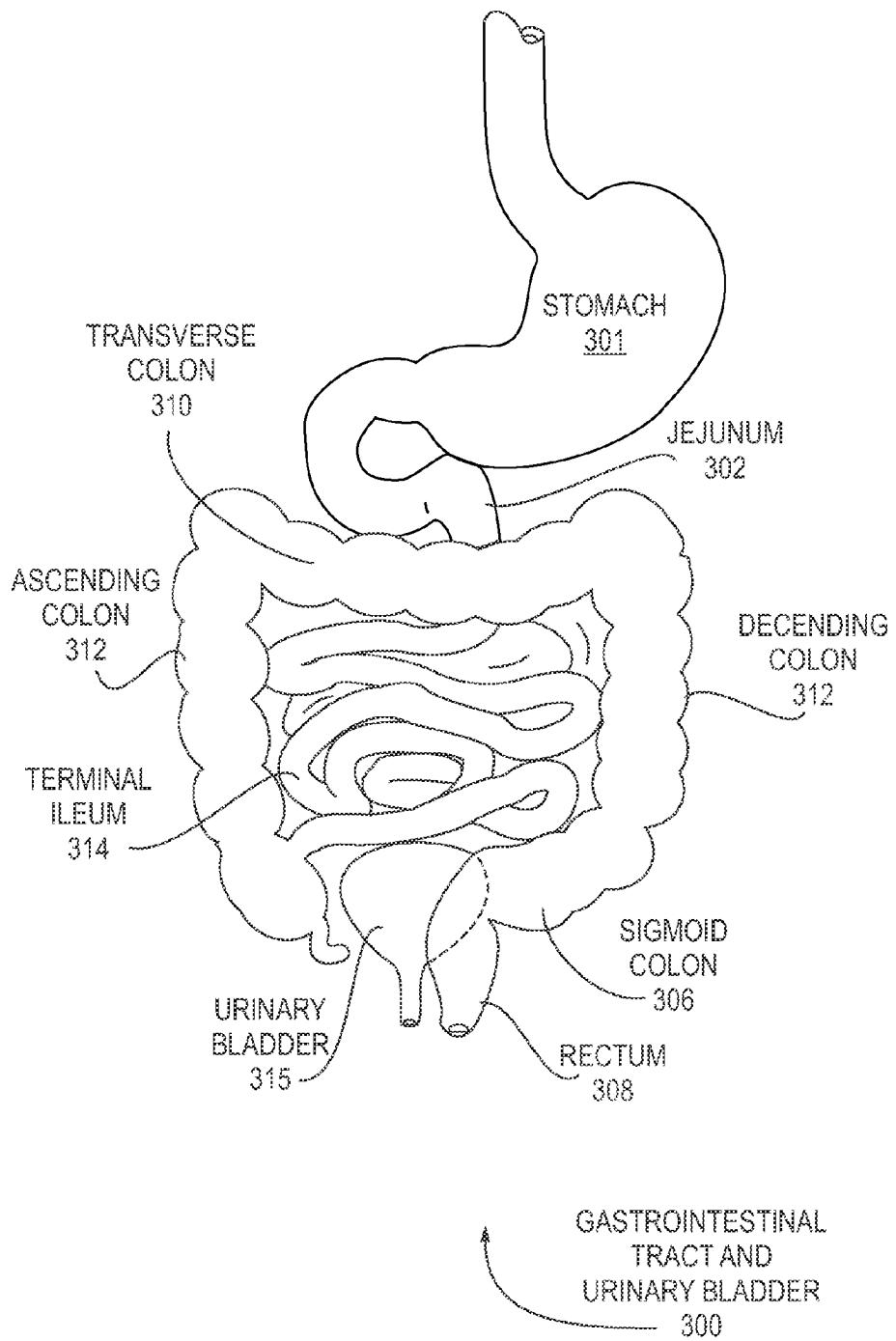
FIG. 3 illustrates a view of the gastrointestinal tract and urinary bladder 300 of a human.

FIG. 3 illustrates a gastrointestinal tract and a urinary bladder system 300 of a human. The figure shows various segments of the gastrointestinal tract, including the stomach 301, the transverse colon 310, the jejunum 302, the ascending colon 312, the descending colon 304, the sigmoid colon 306, the terminal ileum 314, the urinary bladder 315 and the rectum 308. The external sensors or electrodes may be positioned on the skin over the segment of the gastrointestinal trace of interest for acquiring signals from such segment, and/or adjoining portions, of the gastrointestinal tract. When internal sensors or electrodes are used, such sensors may be suitably implanted or anchored to the respective portion of the gastrointestinal tract, for example by means of endoscopy or a swallowable device containing a sensor or electrode.

Figure 4:
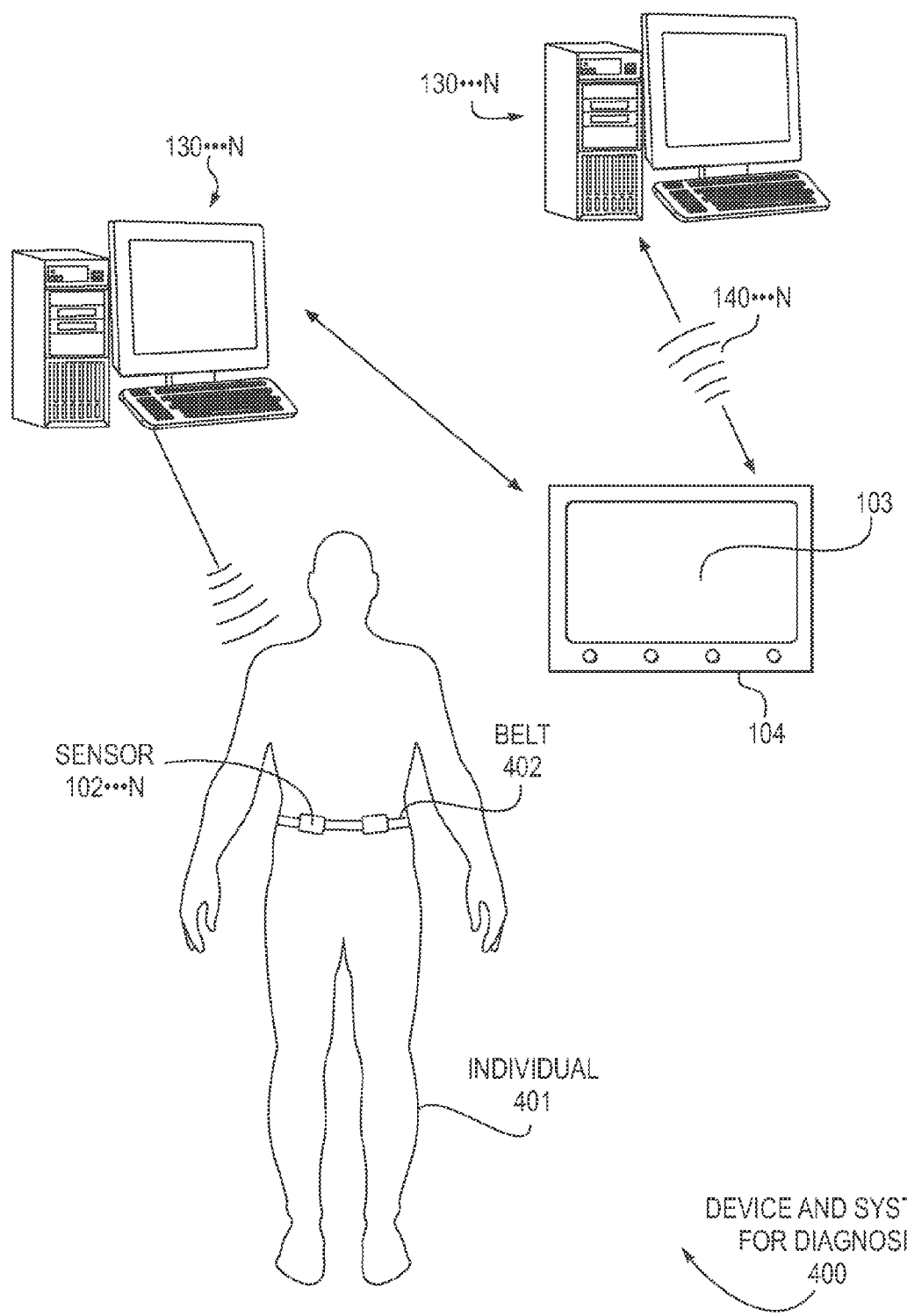
FIG. 4 is a diagrammatic view of the device and system for diagnosis 400 for a human wearing sensors.

FIG. 4 is a diagrammatic view showing a device and system 400 that can be used for diagnosis in a method of the present invention. One such method is for diagnosing disorders of the gastrointestinal tract. In one embodiment, the subject or patient 401 wears a belt 402 like device fitted with one or more sensors or electrodes 102 . . . N. The sensors 102 . . . N can include an internal sensor or electrode. The sensors 102 . . . N can collects various parameters, information or signals from the gastrointestinal tract of the individual 401 and transmits such parameters, information or signals directly or via observation device 104 to one or more of computers 103 . . . N or only to the observation device 104. The observation device 104 or the one or more computers 130 . . . N or the one or more sensors 102 . . . N itself may have the device system 200 embedded in it. The data may be collected, analyzed and used for diagnosis by the physician or the care taker.

Each of the one or more sensors 102 . . . N may be an electrode and can include a microphone, a pressure transducer, a temperature monitor, a strain gauge, an accelerometer, a position tracking device, a wireless transmitter and a wireless receiver, or a combination of any of the foregoing. An electrode or sensor may have the capability to record electromyography, electrocardiography, electroencephalography, skin conductance, electrical signals from gastrointestinal tract or urinary bladder, or any combination of the foregoing.

Each of the one or more sensors 102 . . . N may be a wet or a dry electrode, one end of which is positioned externally on the skin and the other end of which is connected to the observation device 104 and/or any other electrical component of the system 400 either wired or wirelessly. The sensors 102 . . . N may be implanted under the skin or located internally in the gastrointestinal tract and communicate with the observation device 104 and/or any other electrical component of the system 400 wirelessly. The external sensors 102 . . . N can be secured to the body by various means such as sticky pads, strap, belt 402 or similar devices. Alternatively, the external sensors may be part of clothing that is worn by subject. Further, belt 402 can have any suitable array of sensors or electrodes 102 . . . N thereon, for example any of the electrode arrays illustrated in FIGS. 16-19 and described below with respect to FIGS. 16-19.

Additionally, system 400 and all of the others systems herein can include any of apparatus 1601, 1701, 1801 or 1901 described below.

The sensors 102 . . . N, when used as wet electrodes, can be used with a conductive gel disposed between the electrode and the skin of the patient to lower the skin impedence. In another embodiment, any of the sensors 102 . . . N may be a dry electrode that does not require usage of conductive gel. Instead, the contact surface characteristics of the electrode are modified to increase the contact area between the skin and electrode.

The sensors 102 . . . N, can be of different shape and size. The sensors may be passive or active. The sensors may include at least one amplifier, a filter, an analog to digital converter and wireless transmitter or any combination thereof. The sensor may be a simple passive electrode or a combination of accelerometer to record movement of the subject or a part of thereof, skin conductance monitor stress level, position tracking system to determine the physical location of the subject with reference to surroundings, microphone to record sounds of the GI tract, and the like.

In one embodiment, each of the one or more sensors 102 . . . N, may be able to acquire signals related to contractility, pressure, electrical activity of gastrointestinal tract, or pH or chemical composition of the contents of the gastrointestinal tract. The sensor may be secured to the internal wall of the gastrointestinal tract via an endoscope.

In one embodiment, each of the one or more sensors 102 . . . N may transmit data continuously or intermittently onto a memory card in the observation device 104 or to another suitably configured device of the system of the invention, either for further processing or storage. In one embodiment, each of the one or more sensors 102 . . . N may be equipped with memory on board to store the acquired data. In one embodiment, each of the one or more sensors 102 . . . N may be mounted on stretchable belt, such as belt 402 discussed above, that extends around the torso of the patient and can be connected to a piezo actuator, strain gauge or similar mechanism to measure changes in diameter of the chest and/or the abdomen so as to monitor the distension associated with abdominal bloating. In one embodiment, each of the one or more sensors 102 . . . N may be configured to acquire skeletal muscle activity from the abdomen, pelvic floor, diaphragm or other parts of the body The system described in FIG. 4 may be used by the clinician to diagnose various motility related disorders of the gastrointestinal tract, including, but not limited to irritable bowel syndrome, incontinence, intestinal obstruction, nausea, vomiting, bloating, gastroparesis, esophageal disorders, constipation, motility disorders of the gastrointestinal tract in Parkinson's disease and autism, and urinary incontinence.

The following example of a method of the present invention is for the diagnosis of irritable bowel syndrome. Without limitation, the method or aspects thereof can be used for diagnosis of other gastrointestinal conditions including bloating, urinary bladder and fecal incontinence, and various types of constipation. Irritable bowel syndrome is a condition associated with abdominal pain, alterations in the bowel habits, stool form and altered motility patterns of the small and large intestines. Irritable bowel syndrome is often diagnosed based on Rome Criteria (I, II or III), mostly based on the patient symptoms and exclusion of the organic disease conditions. Currently there is no device on the market to diagnose irritable bowel syndrome that is directed at monitoring the motility of the gastrointestinal tract based on electrical activity. FIG. 4 teaches a method and a system to acquire signals from gastrointestinal tract and use the data to diagnose the conditions like irritable bowel syndrome. For the purpose of diagnosis, the user wears the external sensors 102 . . . N, on the abdomen using for example securing device 402 or other apparatus of the present invention. Signals from the small and large intestines are acquired, and processed and analyzed. The signals may be processed and analyzed in real time or stored for processing/analysis at a later time either on the observational device 104 and/or one or more of computers 130 . . . N. In addition to the gastrointestinal tract signals, additional sensors can be positioned to acquire heart rate, respiratory activity, skin conductivity and electroencephalography signals to assess the autonomic nervous system status. Accelerometers and location tracking information related to the patient can be recorded simultaneously. Patient symptom and event recording can allow for input of symptoms such as pain, bloating, cramping, psychological status indicative any stress, physical activities such as eating, drinking and bowel movements through observation device 104 and the input control buttons 106 . . . N. For example, patient can press the appropriate one of the control buttons 106 . . . N, when abdominal pain is experienced. The event can be recorded with a time stamp and allow for comparison with changes in the motility pattern of the small or large bowels in relation to that time point. Data related to any autonomic changes can similarly be compared in assessing relationship of the changes to gastrointestinal tract electrical activity/motility. The data may be recorded for a period ranging from one minute to seven days or longer. Data may be acquired while the patient is stationary, ambulatory or while carrying out day to day activities. Any provided accelerometer is provided is configured to detect movement related artifacts of the patient. When movement is detected that interferes with the gastrointestinal tract or other signals, the system may choose to pause acquiring such data until the movement has subsided. Alternatively, the system may flag the segment of the signals as artifacts and may not be considered for analysis. Data from any position tracking device that is provided may be used to determine for example if the patient is at the dining table or in the bathroom or sleeping so that the gastrointestinal tract signals can be correlated with the corresponding activity.

Figure 5:
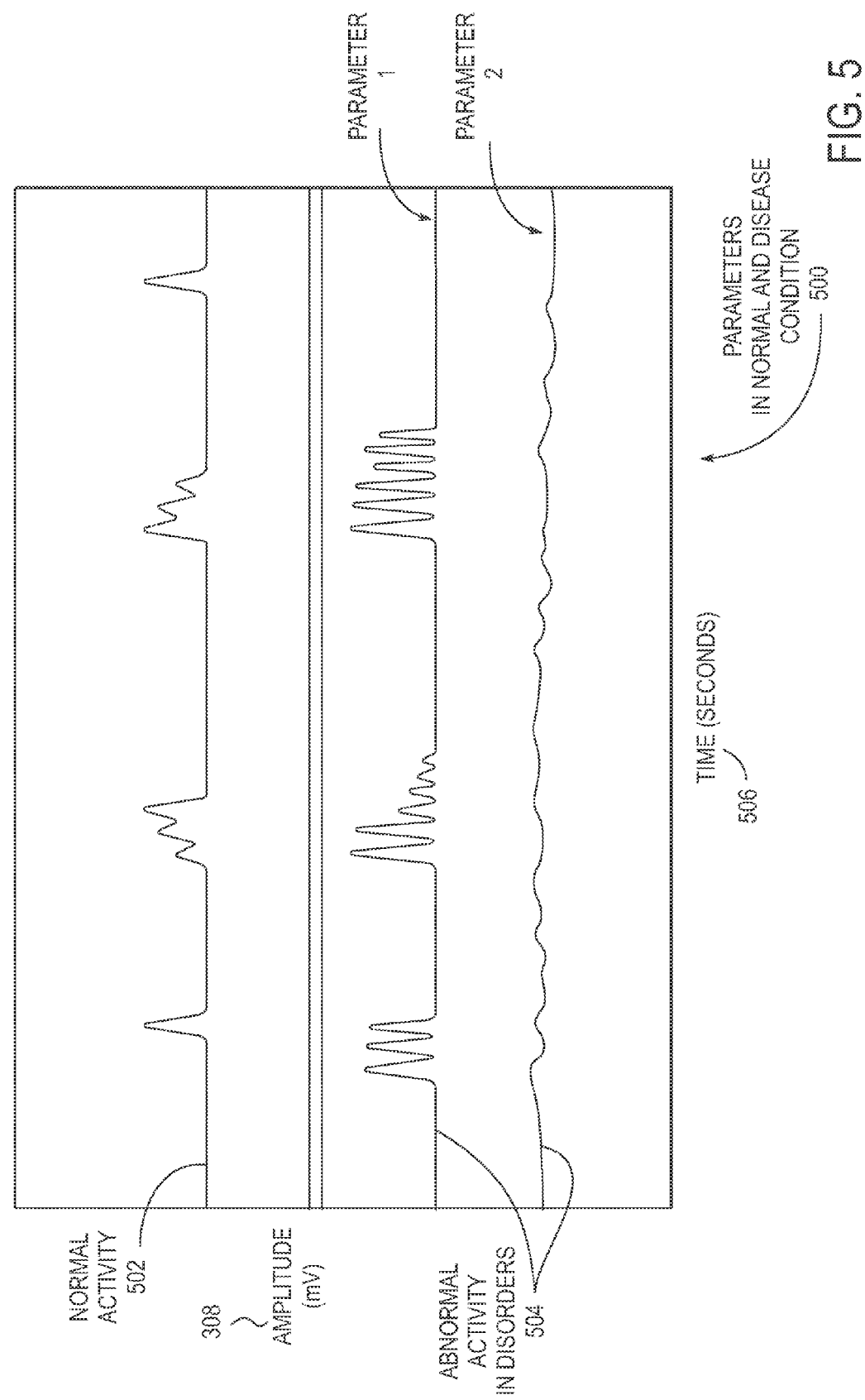
FIG. 5 is a diagrammatic view of parameters in normal and disease condition 500 in an individual.

FIG. 5 shows diagrammatic representation parameters in normal and disease condition 500. The upper wave form is a representation of normal activity 502. In contrast, the lower half shows parameter 1 and 2 as abnormal activities 308 in a disease state. The device of the present invention can identify various wave forms based on various characteristics such as frequency, amplitude, location of the sensor and overall pattern. For example, slow wave signals from stomach can occur with a frequency of 3 cycles per minute (3 CPM), while slow wave signals from lower gastrointestinal tract differ based on whether the signals relate to the duodenum, ileum, colon or other part of the lower gastrointestinal tract. Spike bursts are associated with contraction of the gastrointestinal tract. Spike bursts, amplitude or energy of the slow wave forms may be characterized to correlate electrical activity with the contractility of the gastrointestinal tract. Additionally, wave forms related to interdigestive migrating motor complexes of the gastrointestinal tract, may be also be characterized. The migrating motor complexes usually last from 90 to 130 minutes in normal adults. Other wave forms such as giant migrating complexes which are usually associated with mass movement of the intestinal contents, and are characterized by higher amplitude and longer time, can be characterized. In normal adults the giant migrating complexes occur approximately 6-10 times in 24 hours. Alternations in the patterns of the above wave forms were reported in irritable bowel syndrome patients. For example, increased electrical activity and corresponding contractility of the gastrointestinal tract was observed in animal models of the irritable bowel syndrome as well as in patients using manometry. Therefore, in irritable bowel syndrome patients with predominant diarrhea one could expect increased electrical activity, as represented in Parameter 1 of FIG. 5, and contractions with concomitant increase bowel movement frequency. Similarly, one would expect the opposite in the irritable bowel syndrome patients with constipation predominant symptoms, as represented in Parameter 2 of FIG. 5.

Figure 6:
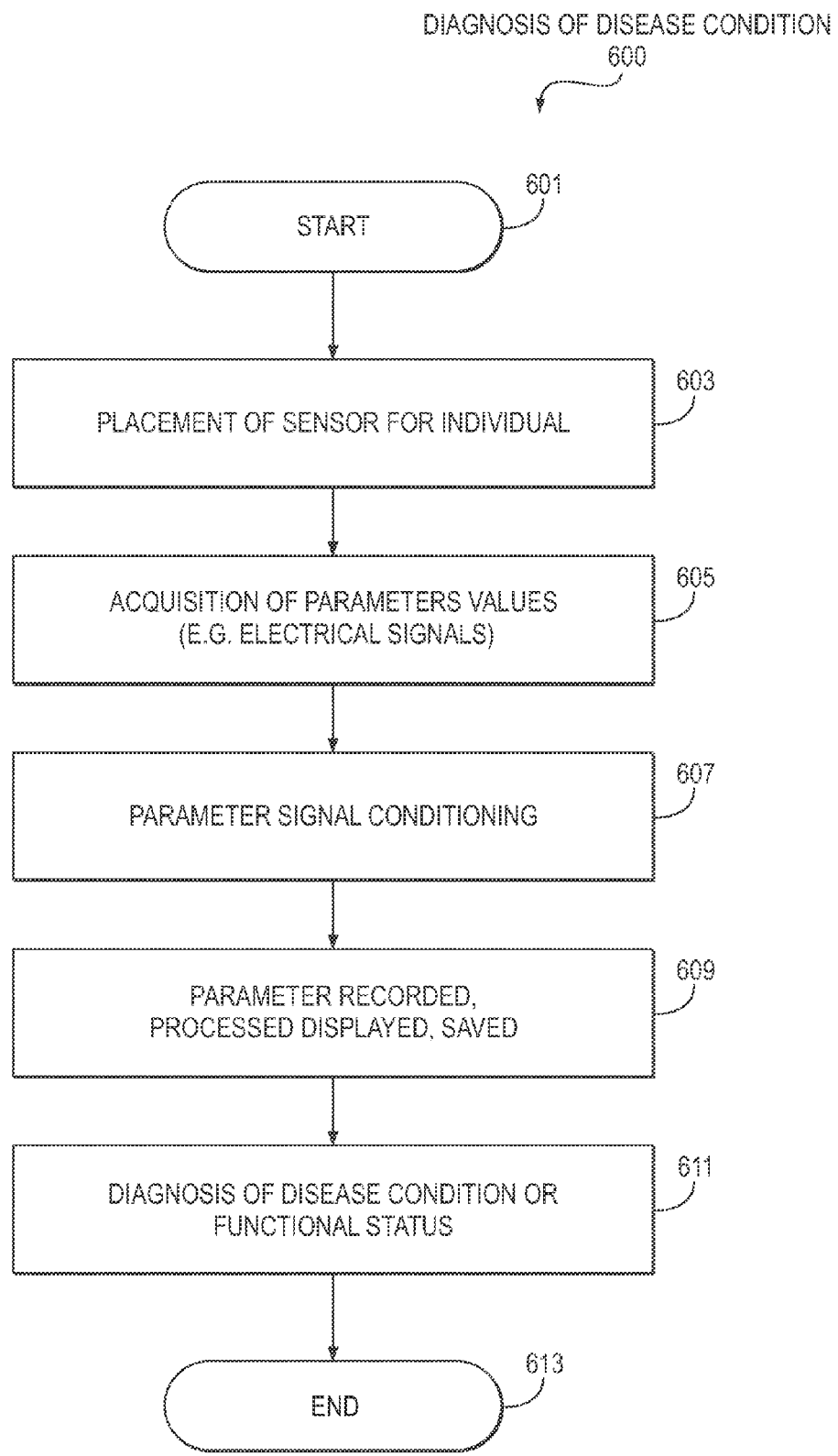
FIG. 6 is a flow chart of diagnosis of disease condition 600.

FIG. 6 is a flow chart showing a process flow for a diagnosis of disease condition 600. The process of diagnosis 600 starts when the powers on the device 601 and secures sensors 603 to the body. The parameter of interest 605, for example electrical signals, can be acquired and conditioned 607. The acquired signal can be recorded, processed, displayed and saved through appropriate sequence of steps 609. Using this information the clinician may diagnose the disease condition 611. The device of the present invention, for example device 104, may integrate the various parameters such as gastrointestinal tract electrical activity, autonomic function, various events and symptoms recorded by the user, and display a comprehensive score for easy understanding. The data may be displayed in graphical or tabular format along with normal baseline values for comparison, for example on display 103 of the device 104. The clinician may consider the presence or absence of various patterns of the gastrointestinal tract, in conjunction with lack of or presence of other symptoms and changes in autonomic activity recorded by the device for arriving at the diagnosis of irritable bowel syndrome. For example, when no organic changes were observed in the gastrointestinal tract, in other diagnostic tests such as endoscopy, X-ray, CAT scan, biopsy, scintigraphy, but a positive correlation is obtained with electrical activity/contractility and symptoms of the patients such as abdominal pain accompanying bowel movements, along with increased autonomic activity recorded from the said device, may help the clinicians towards arriving at the appropriate diagnosis. Once the diagnosis is done this process flow ends 613. Further, the device of the present invention may be useful in monitoring the progression of the irritable bowel syndrome prior to and during or after appropriate therapeutic intervention.

In one embodiment of the present invention, the device may be used to differential diagnosis or monitor the progression of ulcerative colitis and Crohn's disease in a non-invasive fashion. For example, in Crohn's disease patients the slow wave frequency is less frequent and may be absent sometimes, depending on the intensity of the disease condition due to severe scarring of gut segments. This can be differentiated from ulcerative colitis, which is likely presents with increase slow wave frequency, but lower amplitude, compared to the healthy individuals.

In one embodiment, the device and the system of the present invention may be used to acquire electrical signals from the stomach to identify patterns that may be related to disorders such as gastroparesis, which is associated with slow contractility of the stomach, nausea and vomiting, which is associated with increased or abnormal patterns of contraction. Wave forms are characterized in similar fashion as described for irritable bowel syndrome above, and correlated with symptoms and other observations and progression may be monitored using the device.

In one embodiment, the device and the system of the present invention may be used to diagnose and monitor gastrointestinal tract disorders in patients with Parkinson's Disease. The Parkinson's Disease which often is associated with motor dysfunction can also affect autonomic system. As a result, up to 60-70% of the patients with Parkinson's Disease are often affected with a gastrointestinal tract disorder, which can include difficulty in swallowing, gastroparesis, constipation and incontinence. The tremors in these patients can interfere with the proper recording of the electrical activity/contractility of the stomach. Therefore, the accelerometer that can be included in the present invention can be used to identify quiet and non-tremoring periods and record the data from the gastrointestinal tract in those periods for analysis so to accurately diagnose the disorder.

In one embodiment, the device of the present invention may be used in individuals participating in various clinical trials to record changes in the gastrointestinal tract function through recording of signals prior to treatment and during and after the end of treatment with either placebo or a drug.

Additional disorders affecting the gastrointestinal tract, whether or not mentioned herein, can also be diagnosed and managed using the device of the present invention. Such conditions can include but are not limited to gastrointestinal disorders in autistic patients, intestinal obstruction, various forms of constipation and incontinence. Similarly motility abnormalities related to esophageal contractility and acid reflux disease can be identified.

Constipation affects all age groups. In children, the most common cause in a child older than 18 months is their willful avoidance of the toilet. Constipation is a major issue in children with autism. The exact cause is not known, but is most likely due to developmental changes in the central nervous system or to changes in pain perception. The brains of autistic people may not be able to perceive the large intestinal contents and contractions, which is important for initiation defecation process. Constipation is also a major adverse effect associated with several pharmaceuticals on the market and drugs, for example those used for treatment of pain or psychological disorders. Constipation is currently treated using various over the counter medicaments, for example laxatives, fiber supplements and stool softeners, and prescription medications, transcutaneous, neurostimulation and sacral nerve modulation with implantable neurostimulation devices.

Biofeedback techniques can be used for the treatment of various functional disorders of the gastrointestinal tract and urinary bladder, for example constipation related to pelvic floor dysfunction, fecal and urinary incontinence and irritable bowel syndrome. Gastrointestinal tract related biofeedback training for constipation is described in detail in this section. The training may also be used for other disease conditions of the gastrointestinal tract or urinary bladder. The general goal of biofeedback technique is to restore the normal gastrointestinal tract contractility pattern and there by facilitating proper voiding of the gastrointestinal tract contents. The currently available biofeedback options for constipation are based on either inflatable balloons that are placed in the rectum or with use of electromyography recordings from anal muscles or distal part of the gastrointestinal tract to retrain the patients. Both procedures are intrusive or invasive to some extent and require professional healthcare provider supervision. The balloon and anal electromyography electrode-based biofeedback procedures are primary focused on teaching the patient to effectively use diaphragm, abdominal and pelvic floor muscles to push out the rectal contents by straining. In contrast, the biofeedback procedure of the present invention can utilize some or all of electrical signals/contractility recordings from large bowels, electroencephalography recordings and electromyography recordings of the abdominal or pelvic muscles, and skin conductance recordings, to provide biofeedback training to treat constipation. The method teaches the patient to effectively recognize the colonic/rectal sensations, and helps the user initiate and sustain contractility of the gastrointestinal tract, for example the colon and rectum, by helping to overcome the central inhibition and thereby aid in voiding the gastrointestinal tract contents. As the evacuation of the colonic and rectal contents are achieved through movements of the colonic and rectal contents, straining required to push the gastrointestinal tract contents can be minimized. The method of the invention may be combined with other methods of biofeedback training. The device of the invention may enable strengthening of gut-brain axis so that the patient's ability to recognize colonic/rectal sensations is improved on a long term basis. The device can also provide an easy to use, portable, home-based system for use in the privacy of the patient's home without need for professional supervision.

Although the description below is focused on the biofeedback training for constipation, similar procedures can be useful for biofeedback training for bloating, irritable bowel syndrome, urinary and fecal incontinence, and in gastrointestinal disorders in Parkinson's Disease and autism patients.

To facilitate biofeedback training for constipation, the user wears the sensors for recording gastrointestinal tract activity and skin conductivity on the abdomen, and wears headgear 900 to acquire electroencephalography activity. While seated on the toilet, the user may minimize external disturbances by closing eyes and closing doors or may choose to use eye and ear masks to minimize external distractions. The patient is encouraged to practice meditation techniques to focus thoughts on an object of interest, a visualized image or on breathing. The user may be educated on anatomy of the gastrointestinal tract and important role the central nervous system plays in the voiding process. The user is encouraged to focus thoughts on large bowels and on signals related to bowel movement. Signals from gastrointestinal tract, skin conductance and electroencephalography recordings, and the like may be used to provide visual, audio or tactile feedback to the user. This provides a real time feedback on the performance of the user, and reinforces user thoughts and increases the user's ability to recognize any signals from the gastrointestinal tract and improves the learning process. The ability of the user to recognize afferent sensations from the gastrointestinal tract facilitates initiation of gastrointestinal tract activity and contractions, and relaxation of the segments of the gastrointestinal tract distal to the propagating contraction, including internal and external anal sphincters. Continued focus on perceiving the gastrointestinal tract signals from a few seconds to several minutes is required for initiation and sustaining the gastrointestinal tract contractions, to allow the contraction waves to propagate through the end of the gastrointestinal tract to facilitate voiding. The user may use abdominal or pelvic muscles towards the end of contraction phase to aid in complete evacuation of the rectal contents. The user may be trained in the procedure in the healthcare facility or at user's home in their privacy with appropriate audio or video guidance.

Inability of the patients to perceive the signals from the colon and rectum when the contents to be voided are present in these segments often leads to the patient not attempting to void the gastrointestinal tract contents on a regular basis, leading to constipation. Often urge to void results when there is increased contractions, or pressure in the colon and rectal segments. However, in certain people, including children who are unable perceive these urges, for example due to other ongoing activities of higher priority, they fail to bathroom and be seated on the commode to initiate the voiding action, the urge for voiding subsides. As a result they often fail to take advantage of the naturally occurring gastrointestinal tract contractions, to help voiding. Similarly children, of younger age, often get distracted and do not void the gastrointestinal tract contents, which often leads to a vicious cycle of hardening of the fecal material, which makes it difficult for them to void, and the resulting apprehension about the pain related to voiding in turn leads to postponement of the voiding leading to constipation. The device and method described in this application prevents constipation, by alerting the user of the presence of certain either electroencephalography patterns suggestive of perception of the gastrointestinal tract contents in the lower segments. The presence of increased slow waves, spike bursts and giant migrating complexes from lower bowels may be recognized by the device and the user alerted to take appropriate action to facilitate bowel movement. In children with constipation problem, the device may serve to alert the children or the care taker about such gastrointestinal tract activity and keep tract of the number of bowel movements in a day. In patients with diarrhea or incontinence, the device may record such activity to keep track of the status of the bowel movements and the gastrointestinal tract activity.

In one embodiment, the method and device of the present invention may be used to provide biofeedback training to manage constipation in Parkinson's Disease patients and people suffering from Autism Spectrum disorders.

In one embodiment, the method and device of the present invention may be used to assess the gastrointestinal tract motility in patients with paralytic ileus, most often immediately after surgical procedure, mostly related to abdominal organs. Monitoring of the intestinal activity in postsurgical patients is desired to start them on solid oral food.

In one embodiment, the method and device of the present invention may be used to assess abdominal bloating, a condition in which the abdomen feels full and tight. The abdomen may be visibly distended. Bloating can be caused by several factors. including air swallowing, constipation, gastroesophageal reflux disease, irritable bowel syndrome and food intolerance. Patients often feel fullness and early satiety along with flatulence with this condition. Bloating can also be experienced in patients with various gastrointestinal tract disorders associated with psychological behavioral changes. Currently there is no effective means to detect and monitor bloating. The method and device of the present invention may be useful in monitoring and diagnosing the bloating. Bloating can be assessed by acquiring signals from the electroencephalography, electromyography of the diaphragm and abdominal muscles, skin conductivity, and gastrointestinal tract electrical and contractility, or some lesser combination of the foregoing, along with symptoms and patient recorded events. The device may use an abdominal sensor that measures the diameter of the abdomen to assess distension. The bloating symptoms when associated with quantitative and qualitative changes in the autonomic parameters, electroencephalography, electromyography or gastrointestinal tract electrical/contractility activity can be used to diagnose or monitor the bloating condition. The device may also be used for following up on the progression of bloating with treatment.

In one embodiment, the device and system of the present invention may be used to provide biofeedback training to patients suffering from either urinary or fecal incontinence. The urinary bladder incontinence condition affects a significant number of people, especially women. Several causes have been identified and a large number of treatment options including medical devices, pharmaceutics and surgical procedures have been developed over the years. However, the condition remains uncured in a large number of patients. The device and method of the present invention can provide biofeedback training to the patients using electroencephalography signals and electrical signals acquired from urinary bladder using external sensors and by employing various means to distract the user's attention to so as to minimize the user's ability to either recognize signals from the urinary bladder or disrupt the user thought process to prevent user ability to contract the urinary bladder in response to the afferent signals from the urinary bladder. Although, the description is focused on the urinary bladder, it is recognized that the biofeedback training can apply to fecal incontinence as well.

In one embodiment, a method of treatment of the present invention may include isolating a person away from the distractions including but not limited to noise, vibration and visual distractions so that they can focus to recognize the physiological signals from their body. Additional tools, including without limitation eye masks, ears muffs and head phones, may be used. The additional tools or devices may be noise cancelling devices, anti-vibration devices, and visual blockage devices.

For providing biofeedback training for the urinary incontinence, in one embodiment, the device of the present invention may include appropriate means to minimize or modify various sensory stimuli, for example the visual, auditory, tactile and olfactory, with the purpose of distracting the patient's attention. The device may include event recording capabilities and patient's input. For example, when the patient recognizes an urge to go to bathroom to empty the bladder, the urge may be recorded, which can initiate a sequence of tools to distract the patient's attention to delay or stop the impending urge. In one embodiment, the device of the present invention may provide hardware or software driven alerts to notify the individual or the caretaker of certain changes in physiological activities, for example based on the electrical activity and using customized algorithms, that may require attention of the individual or caretaker to take certain action.

In one embodiment, the device of the present invention with the sensors placed on the head, for example by means of head gear, may be able to capture the electrical pattern associated with the recognition the sensation from the various locations in the body, for example the gastrointestinal tract and urinary bladder, or electrical patterns associated with thoughts directed at either initiating, enhancing or suppressing sensations or urges related certain stimuli, for example bowel movements and urge for micturition, through appropriate algorithms and interpretation of the data. Electroencephalography patterns that precede the urge to void urine may be recognized and used to alert the user to take appropriate action, for example either manually or automatically distract thoughts with or without the use of distracting module, to avoid leakage. In one embodiment of the device of the present invention, the device may be able to generate additional actions directly through analysis of the signals so as to distract the individual from recognizing the signals from the organ of interest. For example, a patient with urinary bladder incontinence or incontinence may be distracted from recognizing the urge signals by generating appropriate audio, visual, tactile, physical, thermal, cold or chemical signals to distract the individual from recognizing inappropriate signals from these organs.

In one embodiment, electroencephalography patterns that precede the onset of symptoms of the irritable bowel syndrome, such as abdominal pain or cramping, may be recognized even before the actual onset of the symptoms, and the thought process of the user distracted to prevent onset of the irritable bowel syndrome related signs.

In one embodiment, the device of the present invention may be used to provide biofeedback training to treat the condition of bloat in a patient in a similar manner as described earlier for constipation. For the purpose of biofeedback training, the person acquires electroencephalography, electromyography, skin conductivity, and gastrointestinal tract electrical/contractility and abdominal distention signals, or some combination of the foregoing, and records symptoms and events as mentioned earlier. When the user notices symptoms related to bloating, the user can monitor the changes in electroencephalography, skin conductivity or electromyography of diaphragm and abdominal muscles, or a combination of the foregoing. If the changes are determined to be related to electroencephalography or autonomic system changes, but not completely related to gastrointestinal tract, then the person can practice meditation or mindfulness or other behavioral modification techniques to get relief. The user may make use of audio visual instructions or distraction tools included to achieve the same purpose. Alarm systems included in the device of the present invention may alert the patient about the bloating condition, if certain patterns related to bloating are detected, thereby further helping the user to reinforce the user on the biofeedback treatment.

In one embodiment, a method of treatment of the present invention may include distracting the patient or person from recognizing the physiological signals by generating stimuli, which include but are not limited to noise, visual distractions, tactile stimuli, physical, chemical, thermal and cold stimuli, so that the person does not focus attention on in appropriate physiological signals.

In one embodiment, the method of the present invention can include additional treatment methods such as psychological treatment, physical exercises and meditation techniques. In one embodiment, a script may be written for the individual or patient to hear and follow the steps and get trained to perform a particular physiological function.

Figure 7:
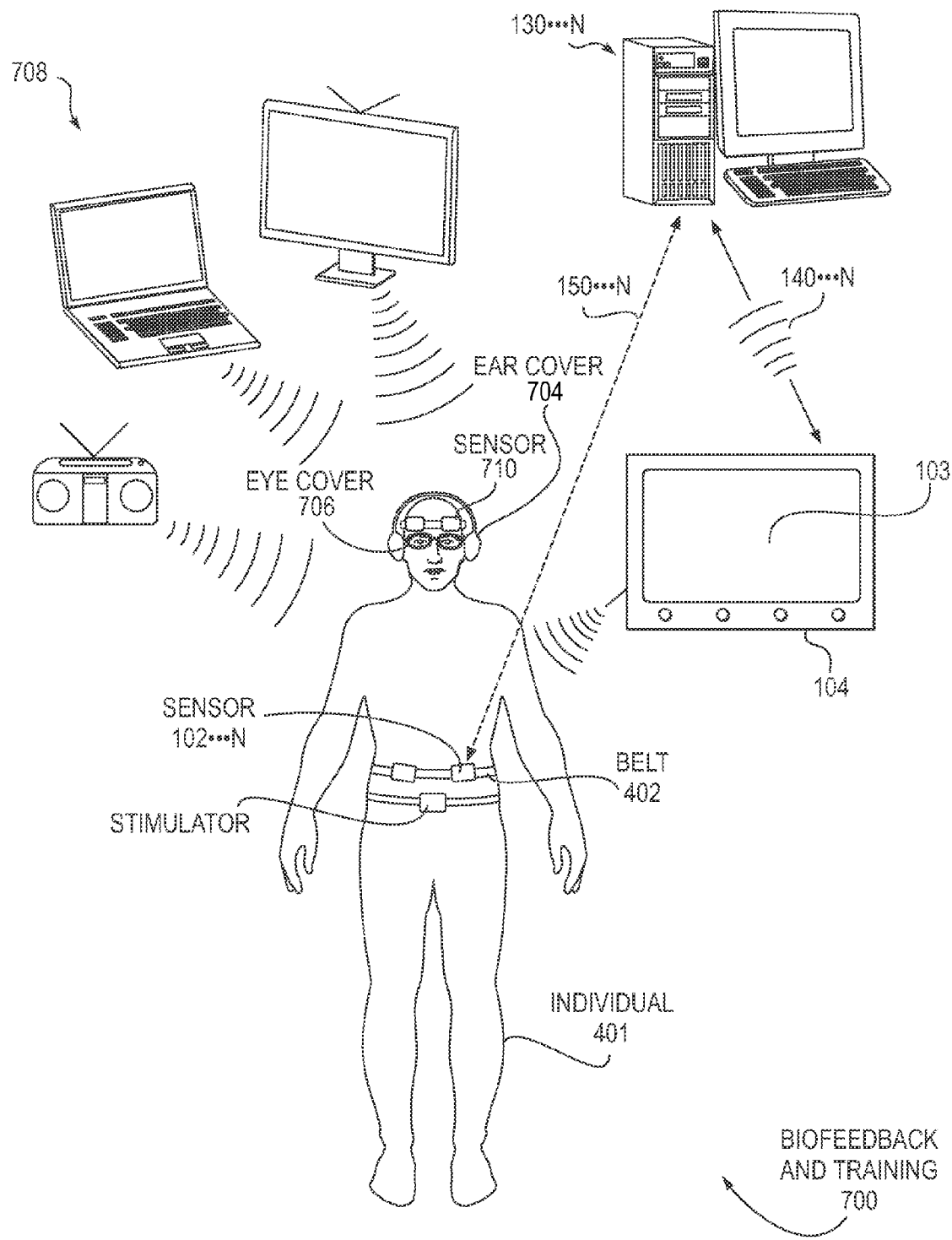
FIG. 7 is a diagrammatic view of biofeedback and training 700 for an individual.

FIG. 7 shows a view of an embodiment of biofeedback and training 700 for an individual using the sensors and device and system of the present invention. The individual 401 can wear a stimulator and a sensor belt to recognize the parameter being displayed on display 103 of the observation device 104. The sensors on the head 710 can register the electrical signals from brain and communicate to a computer readable medium 712. The audio, visual, tactile and focus/distraction inputs 718 can be conveyed to the individual. The individual may wear an eye cover 706 and an ear cover 704 for focusing and not getting distracted to recognize the signals and react to the registered brain activity. This can be effective biofeedback and training for an individual suffering for example from constipation. The individual might use or the caretaker may provide appropriate cues to modify the individual's ability to recognize or distract the individual's ability to recognize certain signals and thereby modify the individual's response to various changes in physiological parameters or stimuli. Such means may include, but are not limited to, eye masks, ear masks, noise cancellation devices, devices to turn off or modify background light and noise or vibrations in the individual's vicinity, devices or agents that modify the sense of taste, smell, touch, devices that create painful or pleasant stimuli, devices to modify audio visual sensations, provide audio-visual inputs or instructions, to prompt individual to perform certain actions or distract the individual from recognizing to ignore certain signals.

As an example, the device can notify the individual about a physiological change (for example, an electrical pattern that suggestive of potential bowel movement, or bladder contraction), which will over the course of time will prompt the individual to learn to recognize or ignore such subtle physiological signals, thereby strengthening the brain-organ interactions over a course of time. The device may display data in various formats and prompt individual to perform certain actions to achieve the targeted goals of modifying the behavior. Such biofeedback device may be used for diagnosing, managing, preventing or treating various disease conditions, including but not limited to managing or preventing constipation, bloating, irritable bowel syndrome and urinary incontinence resulting from over active bladder.

Figure 9:
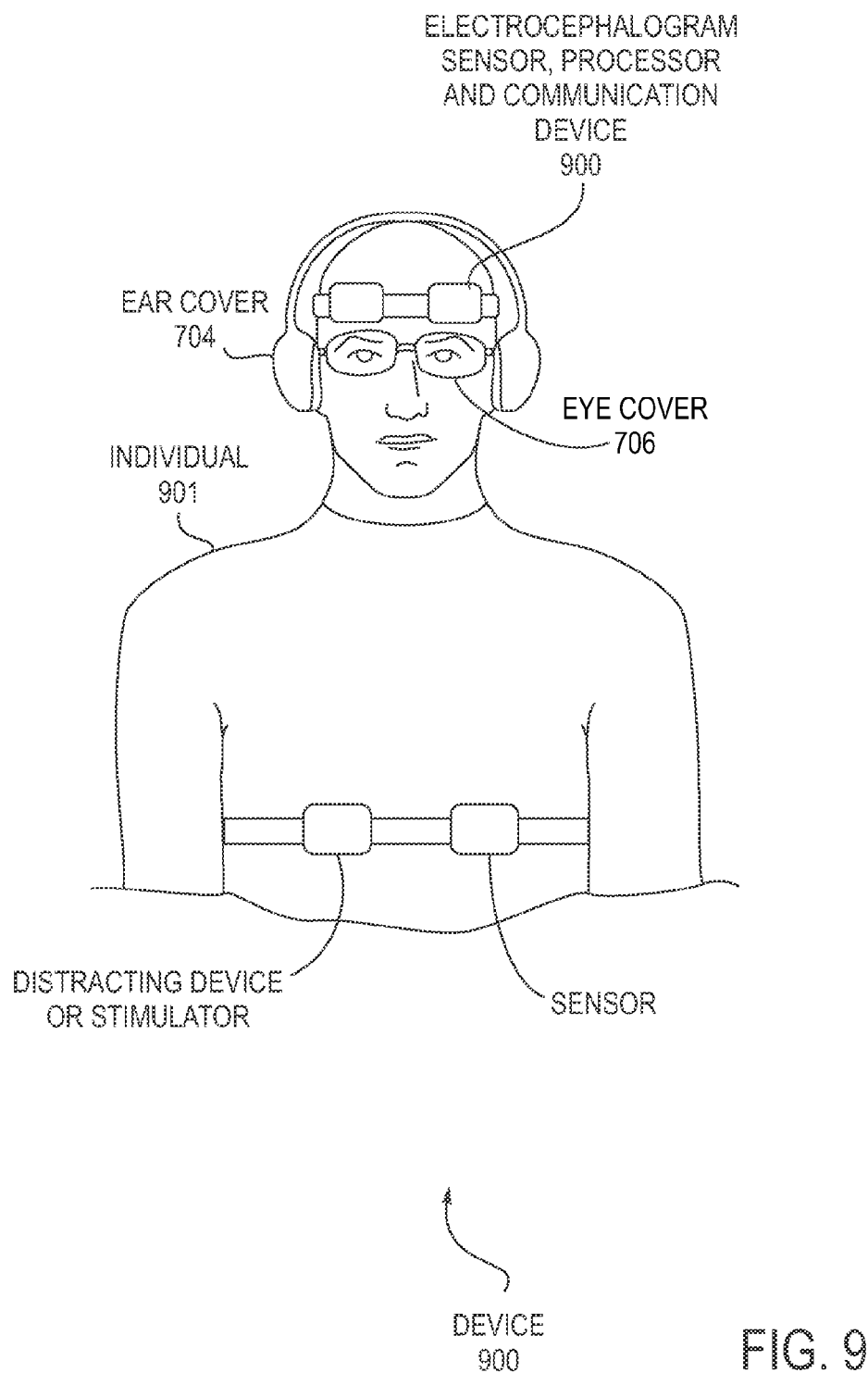
FIG. 9 is a view of sensors and device 900 that may be used helping a person focus thoughts while undergoing biofeedback training.

The individual may also use a head gear to focus further, as shown in the embodiment of FIG. 9. The head gear 902 may also have sensors to record and monitor the appropriate patterns that are generated following recognition of certain changes in physiological signals or stimuli, for example sensations associated with recognition of large intestinal contents, pain associated with intestinal movement, nausea, urge associated bowel movements or urge related to micturition, and fullness feeling associated with bloating condition.

The head gear 902 may be in communication with a display device that is capable of displaying such changes in the thought patterns with the help of graphic individual interface and may provide a means of biofeedback for recognizing and modifying sensations and thoughts associated with various organ systems. Display 103 of observation device 104 is suitable for this purpose. The device therefore acts as a feedback mechanism for the individual to positively or negatively modify the appropriate responses by interacting with the display by using thought patterns that are associated with various organ systems, for example, gastrointestinal, or urinary bladder activity. Such a device may therefore serve as a training tool to strengthen the brain-organ connections in an appropriate manner.

Figure 8:
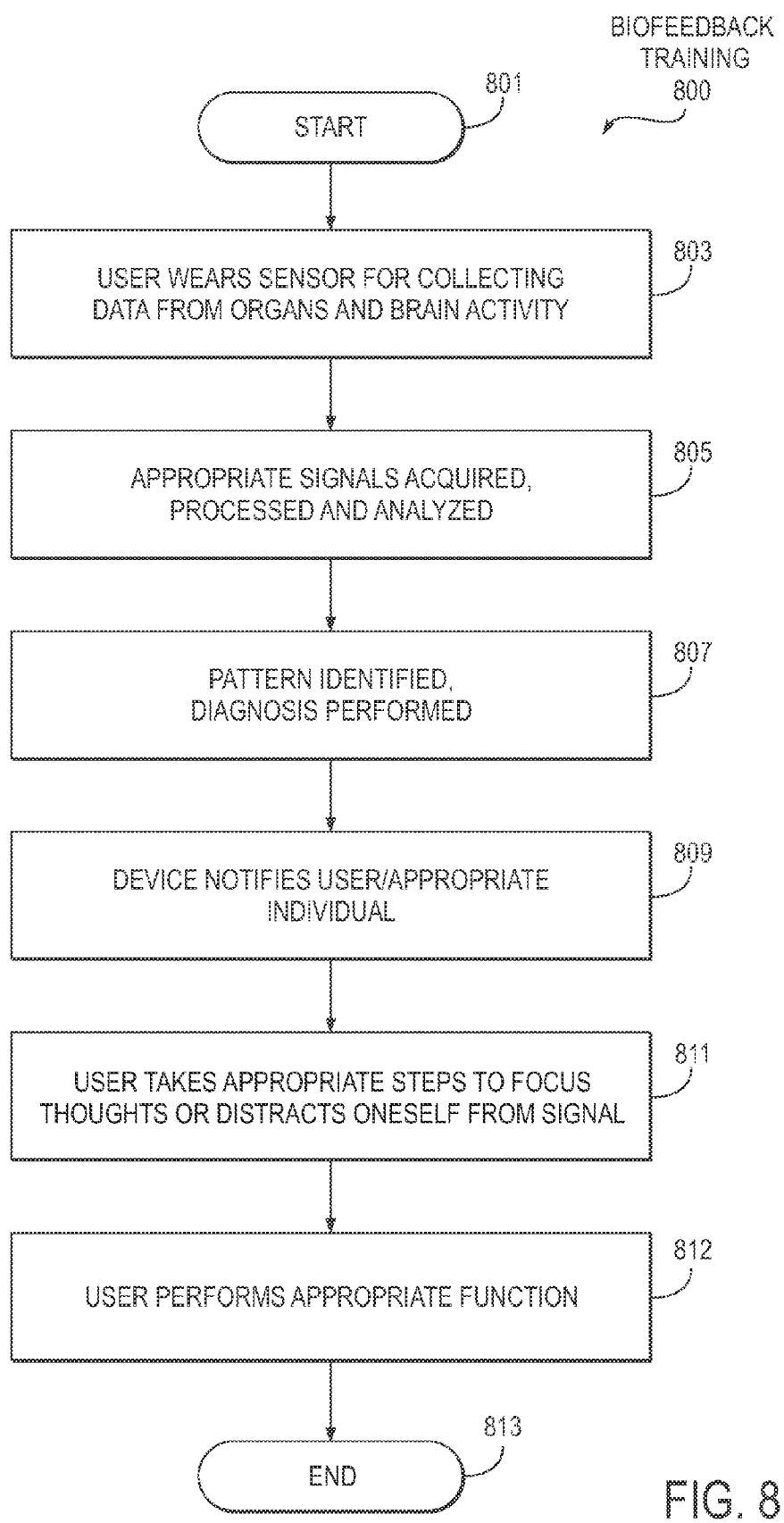
FIG. 8 is a flow chart for biofeedback training 800 for an individual.

FIG. 8 shows a flow chart of the process of one embodiment of the present invention for biofeedback training 800. The individual can wear sensors 803 for collecting data from organs and brain activities. Appropriate signals can be acquired, processed and analyzed 805 and pattern identification and diagnosis can be performed 807. The device can notify the appropriate individual 809 so that they can take proper steps such as assisting the individual or informing the individual or enabling the individual to take proper steps. The individual can then take proper steps to focus thoughts or distracts one from the signal 811 and accordingly the individual performs the appropriate task 812.

Figure 10:
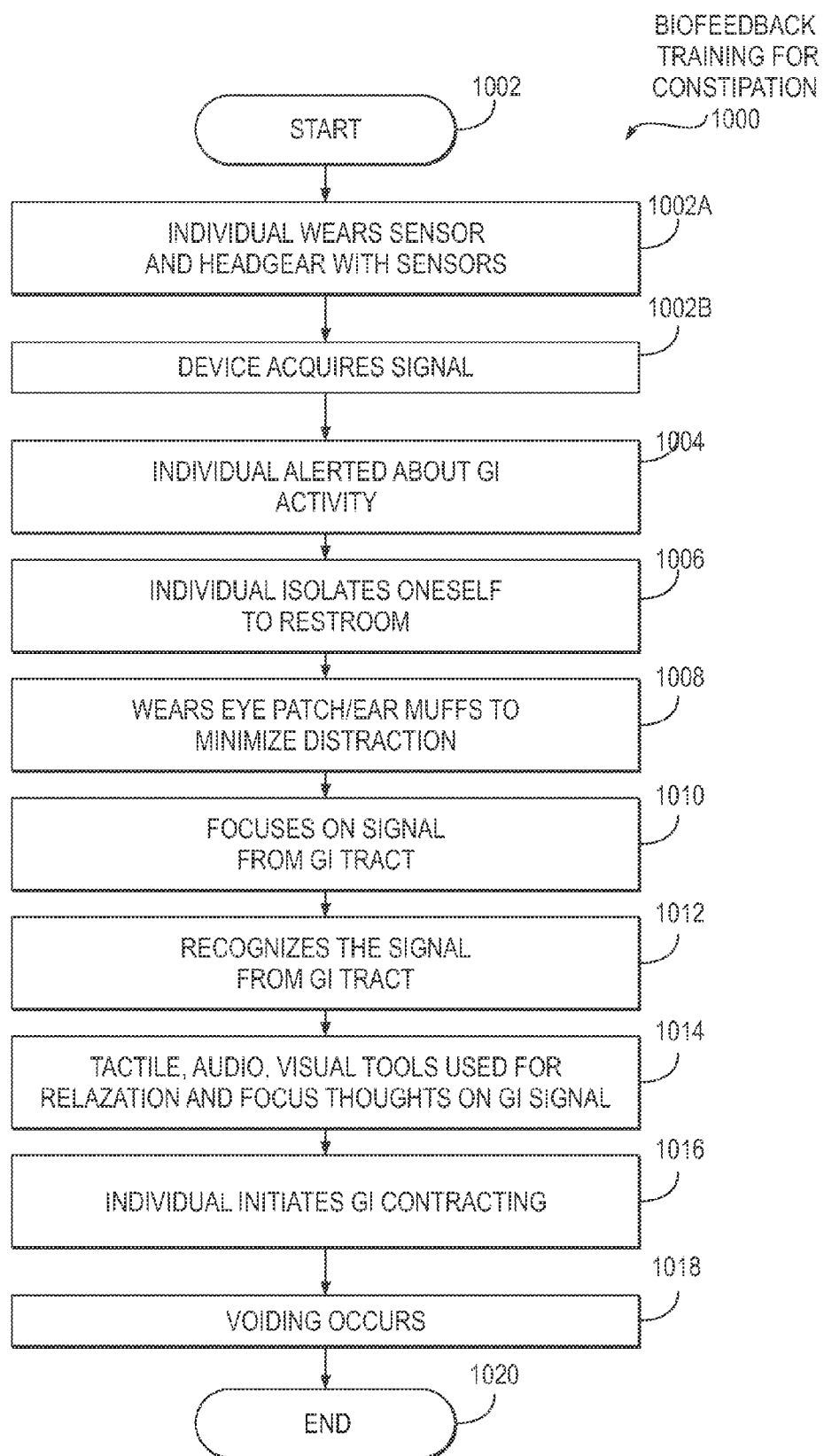
FIG. 10 is a flow chart of biofeedback training for constipation 1000.

FIG. 10 is a flow chart of one embodiment of the present invention for treating an individual for constipation by using a process called biofeedback training for constipation 900. An individual can wear sensor and head gear 1002A and the device can acquire signal 1002B. The individual is alerted about the gastrointestinal tract activity 1004. Individual isolates oneself to rest room 1006. The individual then wears eye patch and ear muffs to minimize distraction 1008. The individual then further focuses on the signal from the gastrointestinal tract 1012. If the individual still feels stressed, tactile, audio, visual tools are used for relaxation and focusing 1015. Individual once concentrates and initiates gastrointestinal tract contraction 1016. As a result voiding occurs 1018. This process is useful, for example, for severely constipated individual or people who have taken medication for some other treatment such as morphine and individuals who have undergone surgery and have very little abdominal strength.

Figure 11:
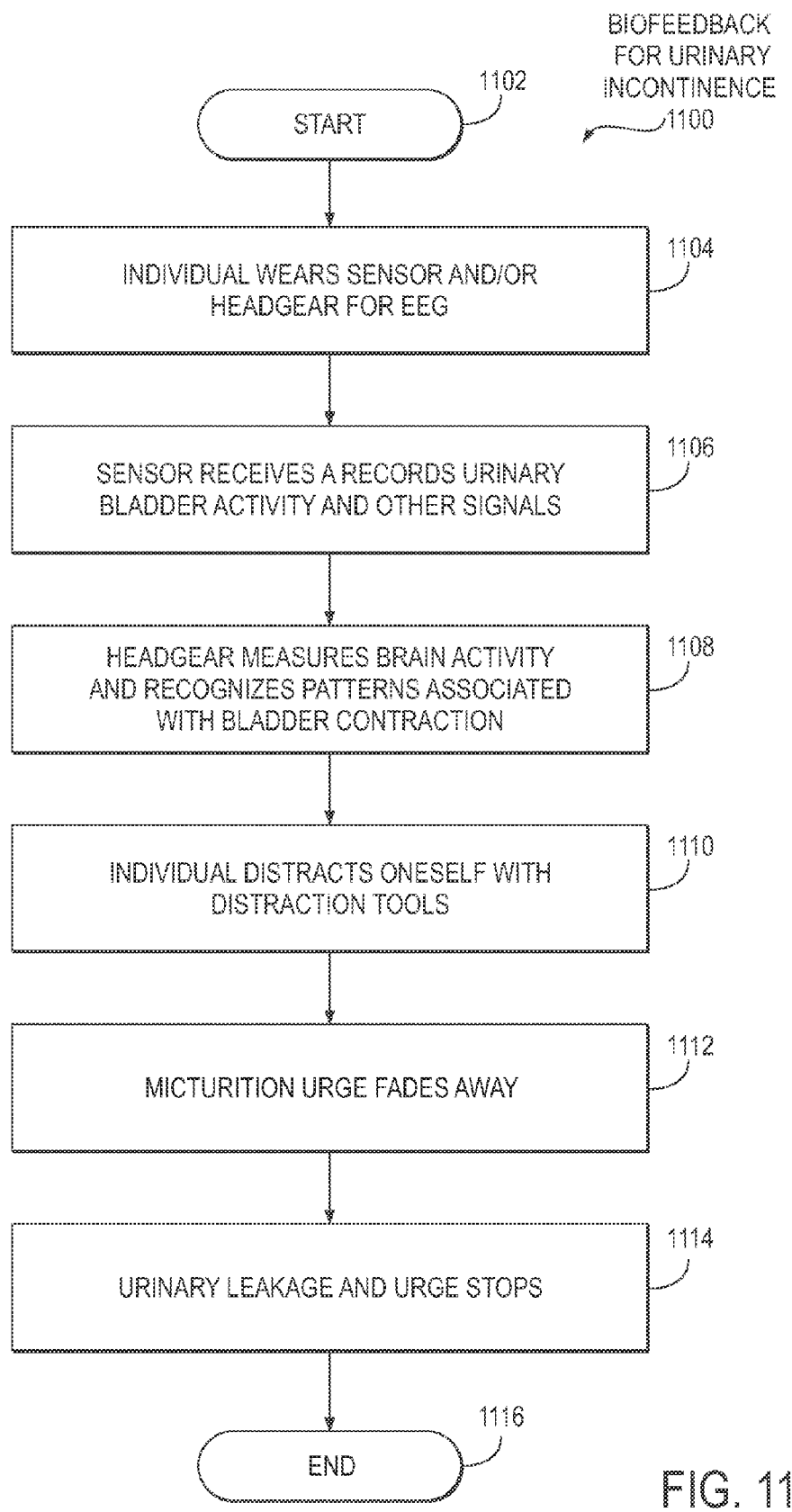
FIG. 11 is a flow chart for biofeedback training for urinary incontinence 1100 using head gear.

FIG. 11 is flow chart of one embodiment of the present invention for biofeedback training for urinary incontinence 1100. An individual wears a sensor and head gear for electroencephalography 1104. Sensor receives urinary bladder activity and other signals 1106. Simultaneously the head gear measures the brain activity 1008 and recognizes patterns associated with urinary bladder contractions. The individual distracts oneself with distractible tools 1110. As soon as the individual takes step 1010, the micturition urge fades away 1112 and the urine leakage stops 1115. This process helps the individual to prevent accidental urine leakage and uncomfortable situations.

Figure 12:
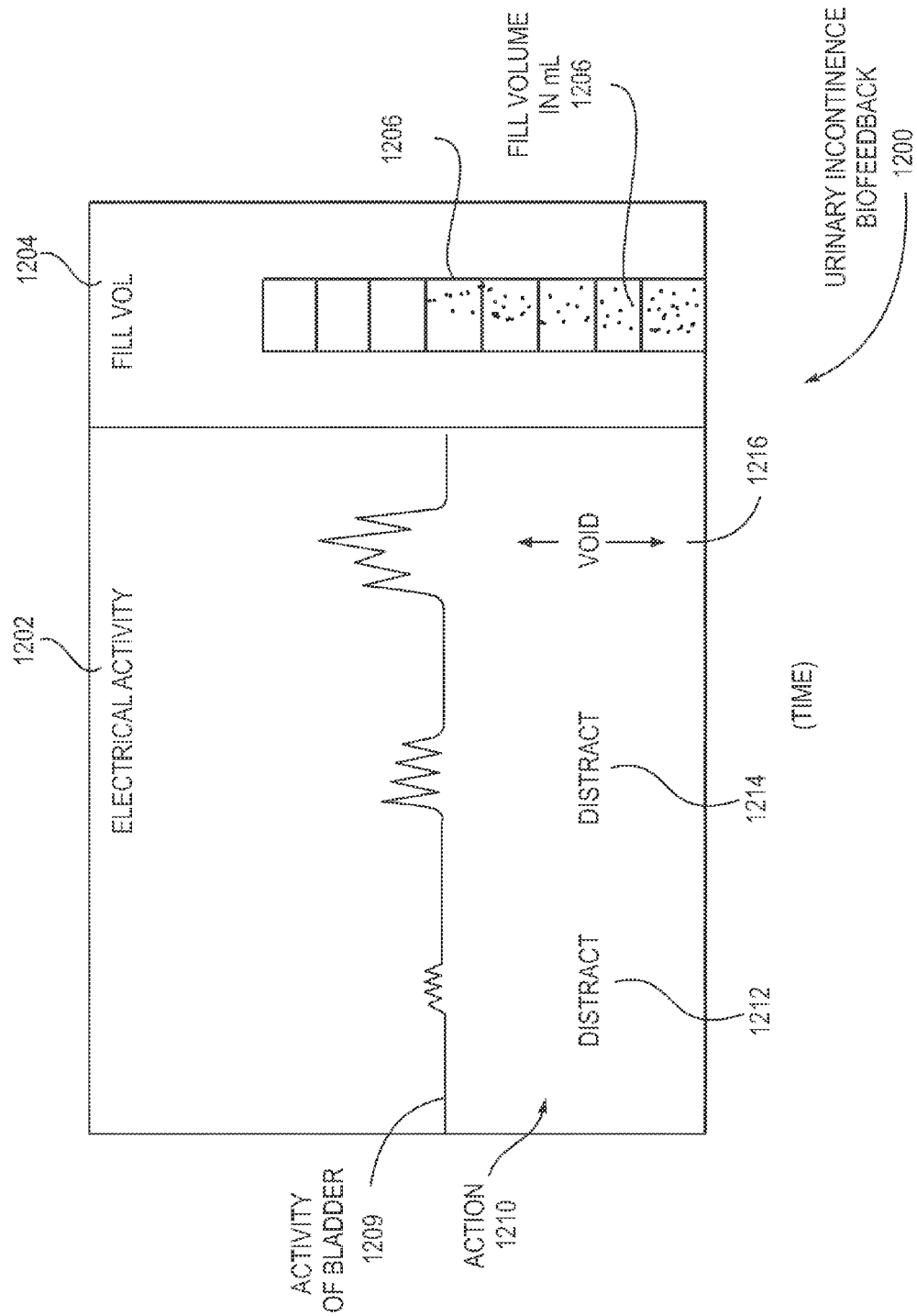
FIG. 12 is a graphical view of the urinary incontinence biofeedback 1200.

FIG. 12 shows a diagrammatic illustration of one embodiment of urinary incontinence feedback 1200 of the present invention. Changes in the electromyography of the urinary bladder detrussor muscle can be displayed with the intravascular pressure and the fill volume 1206. The graph can be shown with other parameter and displayed on the display 103 of the observation device 104. The display can provide the current status of the urinary bladder and the data can be used for providing biofeedback training to the patient or alert the health care provider.

Figure 13:
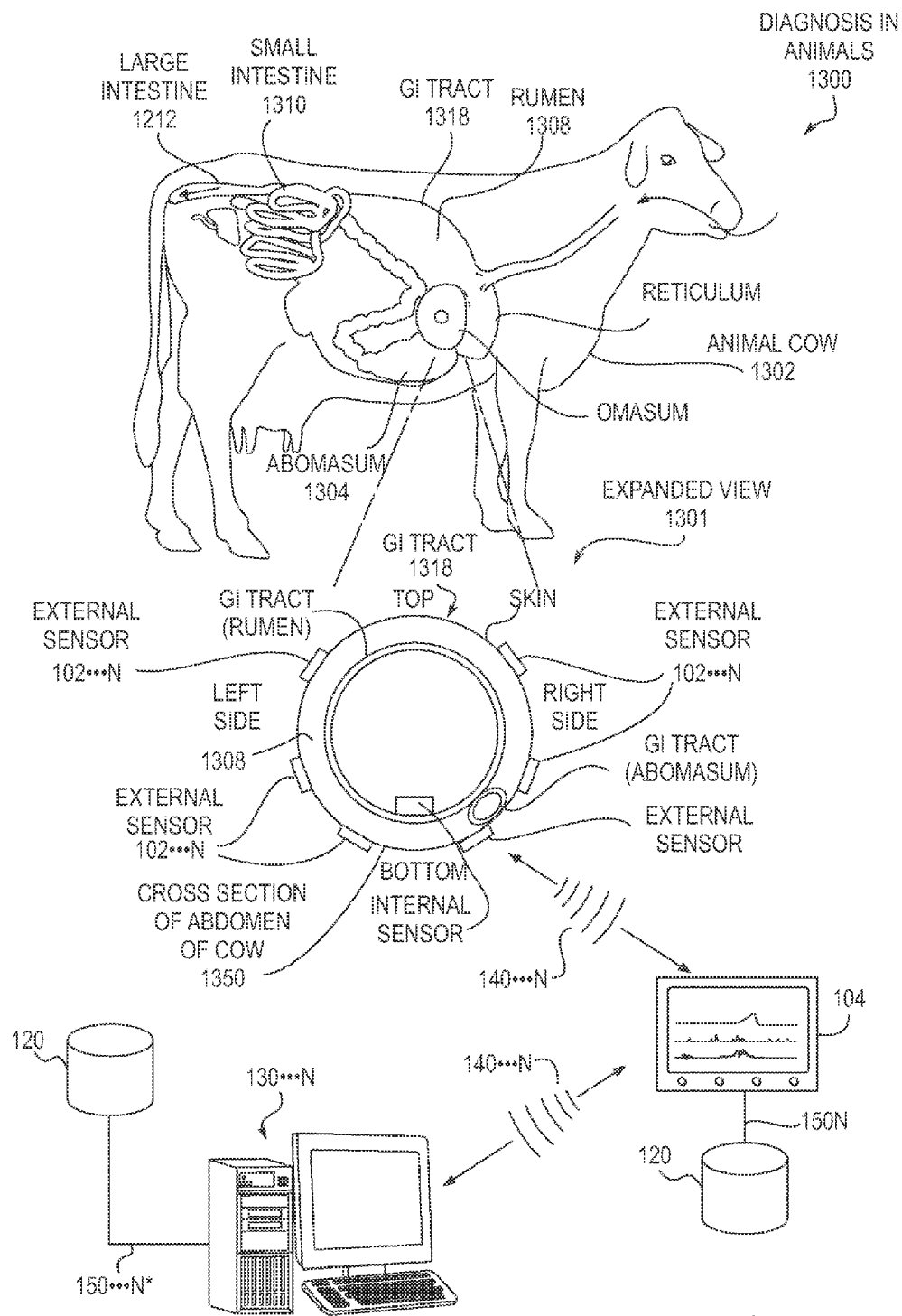
FIG. 13 is a view of diagnosis in animals 1300 with multiple sensors.

FIG. 13 shows one embodiment of the use of the device and system of the present invention for animal use. The device may be used for detecting gastrointestinal tract abnormalities in laboratory animals such as mouse, rat, rabbit, dog and monkey to assess the potential functional changes in gastrointestinal tract following administration of pharmaceuticals. The device may also be used for diagnosis of gastrointestinal tract abnormalities in pet animals as well as farm animals. The device and system can be used for diagnosis in animals 1300 using the sensor and observation device connected to a network. The sensors can be implanted inside or attached outside the animal and in one embodiment are positioned around the gastrointestinal tract. Each sensor 102 . . . N may record and transmit signals to the device 104 or to one or more of the computers 103 . . . N. Depending on which section, for example abomasum is transmitting signals at a larger rate than the rumen the physician may diagnose that some abnormality is happening inside the cow and immediate help may be needed. Position specific signals or total signals from the gastrointestinal tract are indicative of a certain disorder and may be used to obtain the proper diagnosis. The internally and/or externally placed devices may be useful in monitoring various physiological parameters and disease conditions, including but not limited to motility of stomach and large and small intestines, rumen, reticulum, omasum and abomasum, bloating of the rumen, left or right sided displacement of abomasum, traumatic reticuloperitonitis (hardware disease) or pericarditis, urinary bladder related pathologies, pregnancy status, condition of the fetus and the dam, and prediction of delivery time. For example, abomasal displacement may be diagnosed based on the direction of the signal in relation to the sensor, amplitude of the signal in relation to the sensor. The signals from the patients (animals) are compared with signals from normal animals for the diagnosis of the condition.

Figure 14:
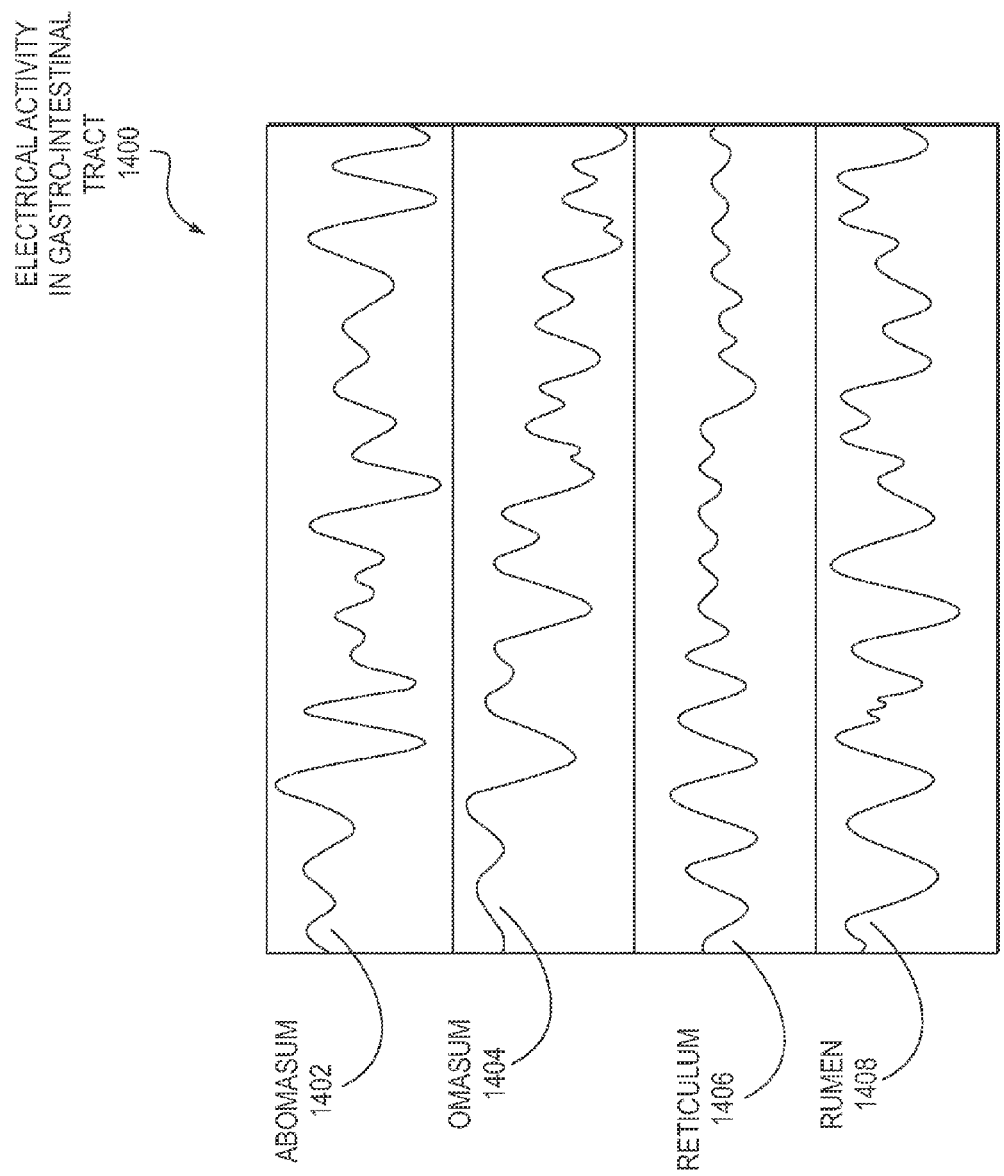
FIG. 14 is a graphical display of gastrointestinal tract electrical activity of animals 1400.

Electrical activity in the gastrointestinal tract 1400 is illustrated in FIG. 14, and includes the activity in abomasum 1402, omasum 1404, reticulum 1406 and rumen 1408.

Figure 15:
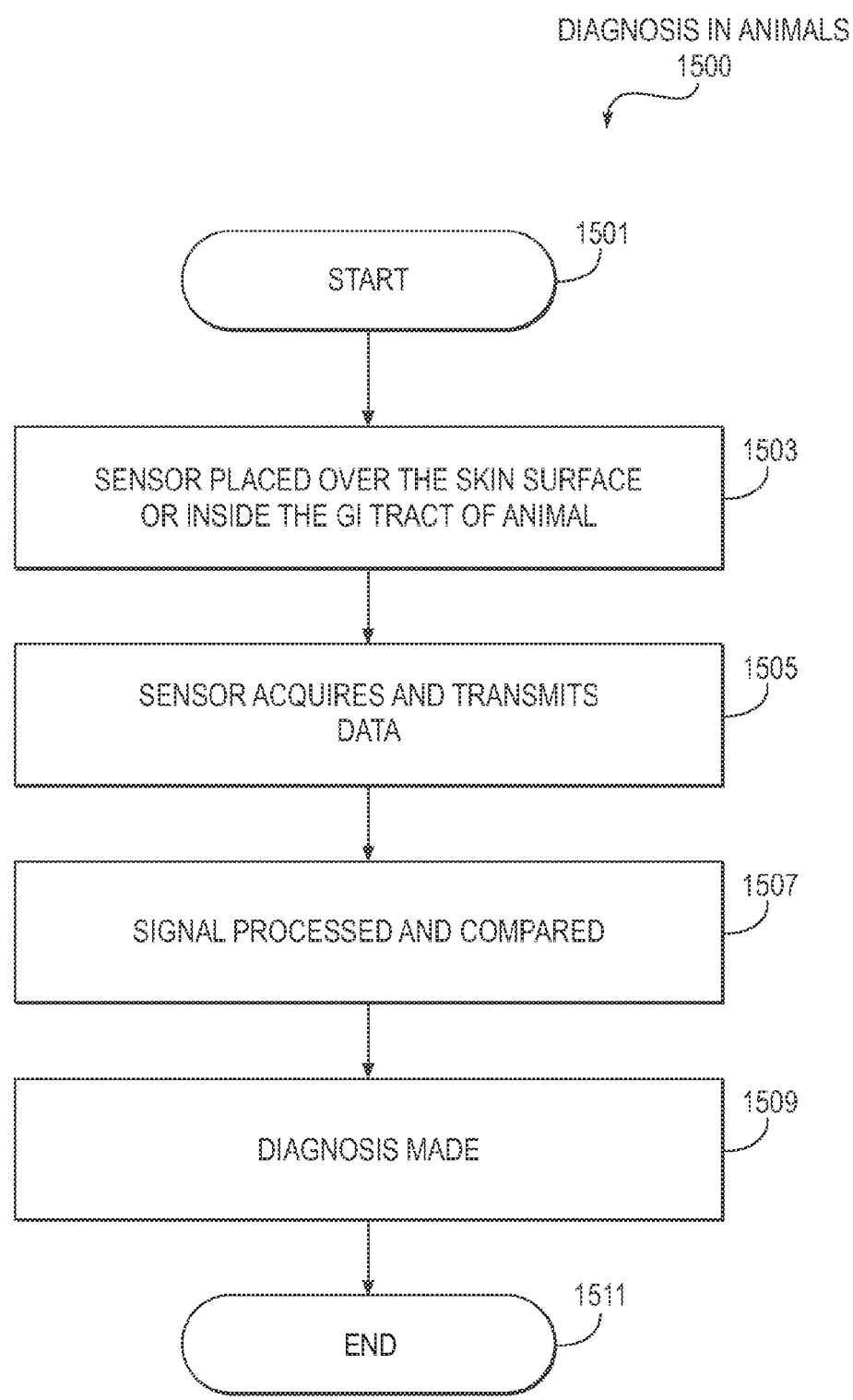
FIG. 15 is a flow chart showing flow chart for diagnosis of gastrointestinal disorders in animals 1500.

FIG. 15 shows a flow chart of one embodiment of the present invention for the diagnosis in animals 1500. After start 1501, sensors are placed either inside or outside of the animal 1503. Signals are acquired and transmitted 1505. Diagnosis can be made 1509 based on signal processing and comparison of the acquired signal 1507.

Arrays of sensors 102 . . . N can be placed on a flexible supporting structure made of flexible polymer, fabric, or a mixture there of to conform to the contours of the body, and provided with belts, straps, clips, glue, Velcro, hooks, buttons and other means to secure to the torso. The following FIGS. 16 to 19 illustrate examples of various embodiments of a flexible sensor array on a supporting structure for acquiring signals from various segments of the gastrointestinal tract such as the colon, rectum, esophagus and stomach. The sensor arrays allow for choosing various combinations of electrodes to configure the signal acquisition with respect to the specific selected organs. It is appreciated that similar or other arrays of electrodes or sensors can be provided with other organs or segments of organs in a human or other mammalian body.

Figure 16:
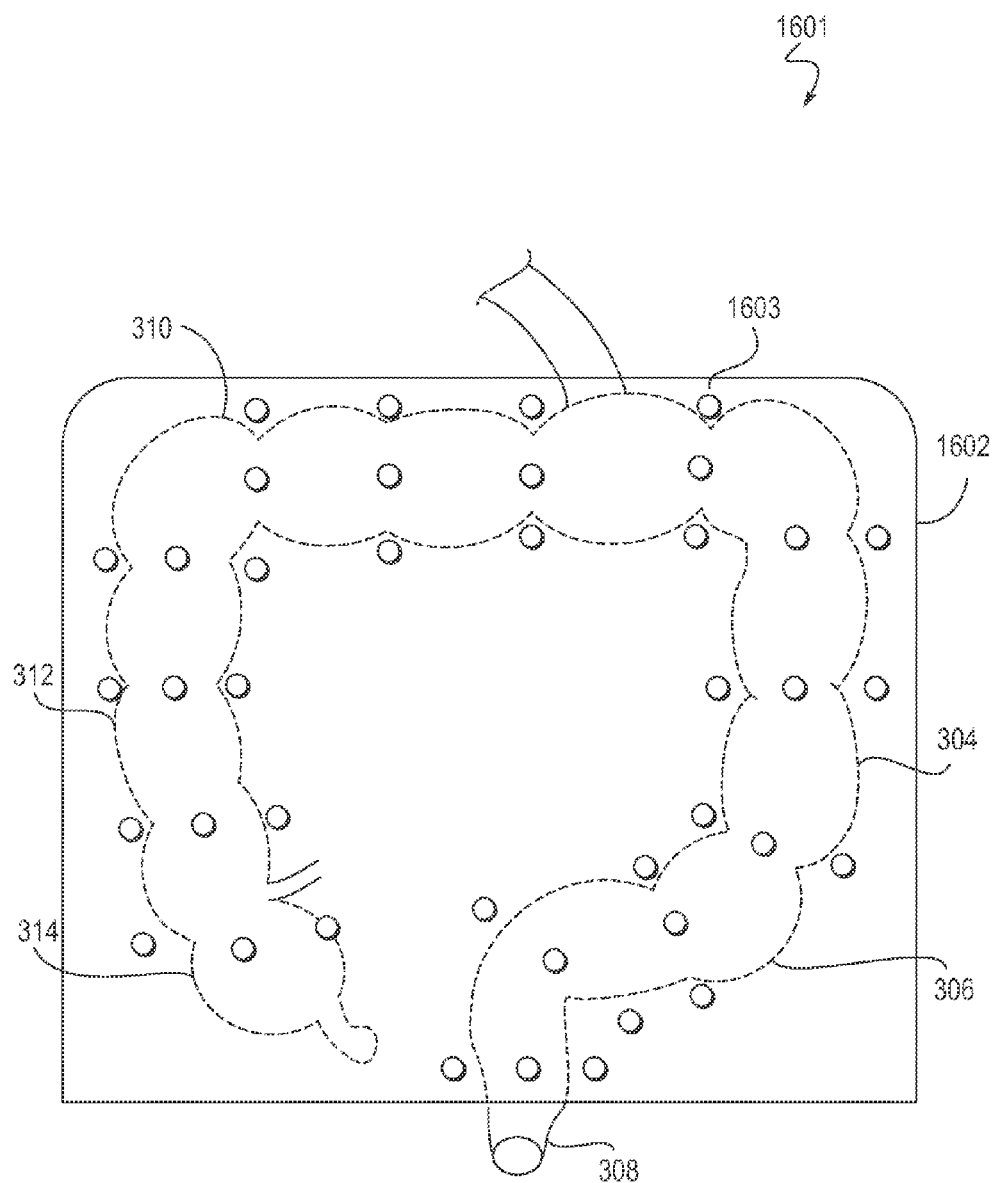
FIG. 16 is a schematic plan view of an embodiment of an apparatus having an array of external electrodes on a support structure for recording signals from the colon and rectum.

In one embodiment of an apparatus for use in diagnosis or treating disorders of the gastrointestinal tract of a mammalian body such as a person, illustrated in FIG. 16, an apparatus 1601 is provided that can include a support structure 1602 for placement on the skin of the body overlying any suitable segment of the gastrointestinal tract, for example the colon and rectum. The support structure can be made from any suitable material, and in one embodiment is made of a flexible sheet which can be formed from one or more layers of plastic. A plurality of electrodes or sensors 1603 are carried on the support structure 1602 and positioned relative to each other on the support structure in a suitable array 1604 so as to follow the shape of the colon and rectum. A suitable colon and rectum are shown in dashed lines in FIG. 16. In the illustrated embodiment, electrodes 1603 are provided on the sheet 1602 for registering or overlying the terminal illeum 314, the ascending colon 312, the transverse colon 310, the descending colon 304, the sigmoid colon 306 and the rectum 308. Although the illustrated array 1604 is shown having sets of three electrodes 1603 spaced along the length of the colon and rectum, other configurations or electrodes 1603 can be provided in the array 1604. For example, the array 1604 can include only one electrode, or two electrodes 1603, at each location on the colon and rectum, and thus the array can consist of a plurality of single electrodes spaced apart along the length of the colon and rectum. Other electrode arrays can be provided for registering with less than all of the colon and rectum, for example any desired segment of the colon and/or rectum.

The array 1604 of electrodes 1603 are thus being capable of recording electrical signals from the colon and rectum, when the apparatus 1601 is placed on the skin of the patient so that the array 1604 is registered with the desired portions of the colon and/or rectum, over an extended period of time.

In apparatus 1601, the support structure 1602 may include a securing structure such as a belt (not shown) for attaching the apparatus to the patient. Other securing structures such as velcro strips (not shown) can extend from the structure 1602 of securing the apparatus to the patient. The support structure 1602 may include an adhesive (not shown) over all or a portion of the underside of the sheet 1602 for securing the support structure to the skin of the body. At least one of the plurality of electrodes 1603 may include an accelerometer (not shown) for detecting motion of the patient. The electrodes 1603 and any accelerometer are electrically coupled by any suitable means, such as by wires, cables or wireless transmitters and receivers, to a suitable electronic apparatus or device, such as portable electronic device, for recording, and optionally analyzing and displaying, the electrical signals from the colon and rectum detected by the electrodes 1603.

Figure 18:
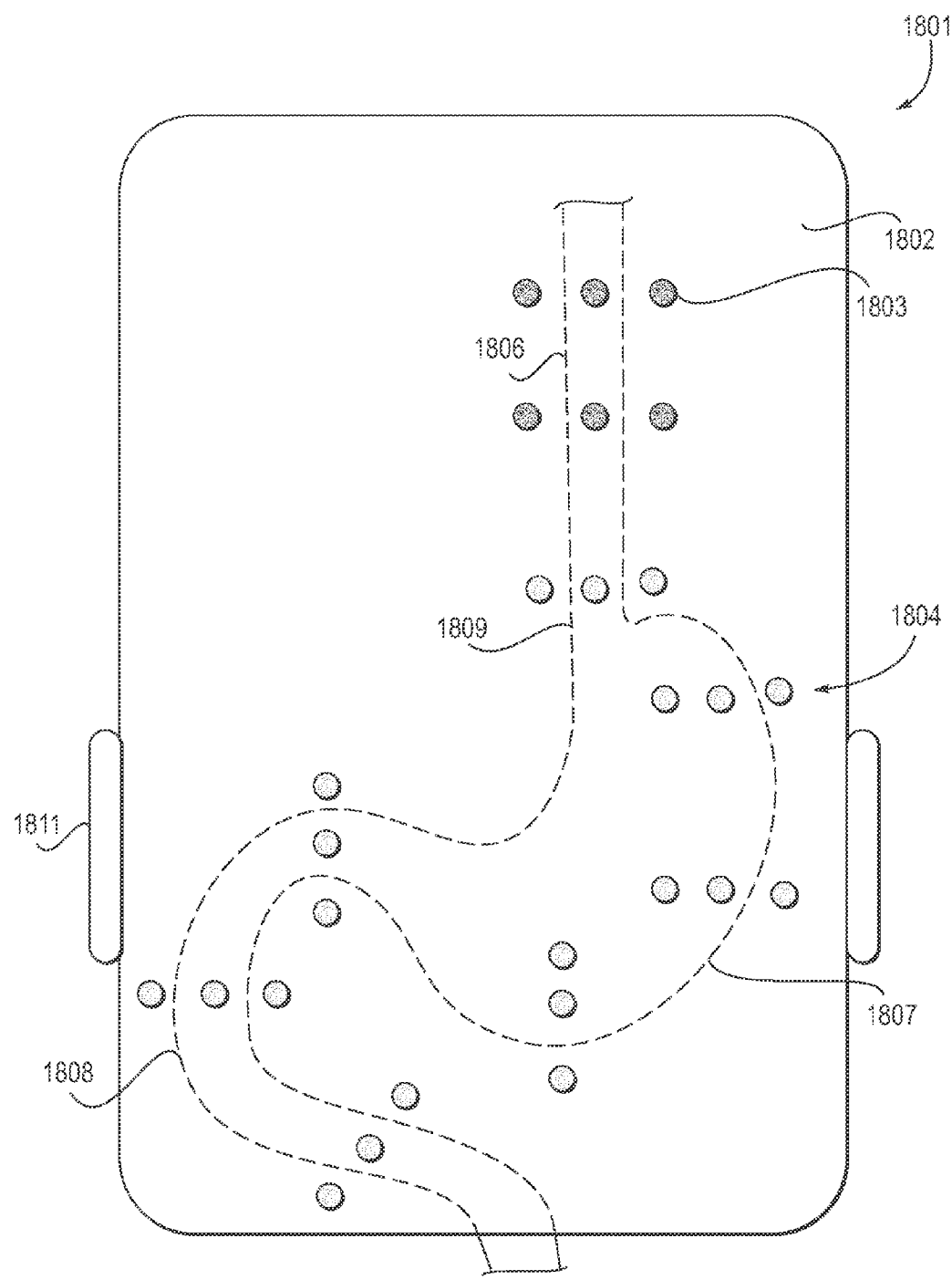
FIG. 18 is a schematic plan view of an embodiment of an apparatus having an array of external electrodes on a support structure for recording signals from the esophagus, stomach and duodenum.

Each of the electrodes 1603 can be any of the sensors 102 . . . N described above. The electrodes 1603 are placed on the support structure 1602 so to extend, externally of the body, along the length of the colon and rectum. When multiple sensors 102 . . . N or electrodes 1603 are so used, the sensors or electrodes may be strategically arranged, for example in sensor array 1604, on the body and allow for acquiring signals from all sensors at once or from only a few at a time. Sensors or electrodes that are strategically placed above certain location on the body may be selected, for example along the length of the colon including ascending, transverse and descending colon as illustrated in FIG. 16 or along the esophagus or body of the stomach as illustrated in FIG. 18, so as to record the sequential propagation of electrical activity from the respective segments of the gastrointestinal tract. When recording gastrointestinal tract electrical activity, the sensors or electrodes arranged in certain pattern may be selected, for example circular pattern, so as to reduce the heart or respiratory interference with the signal.

Figure 17:
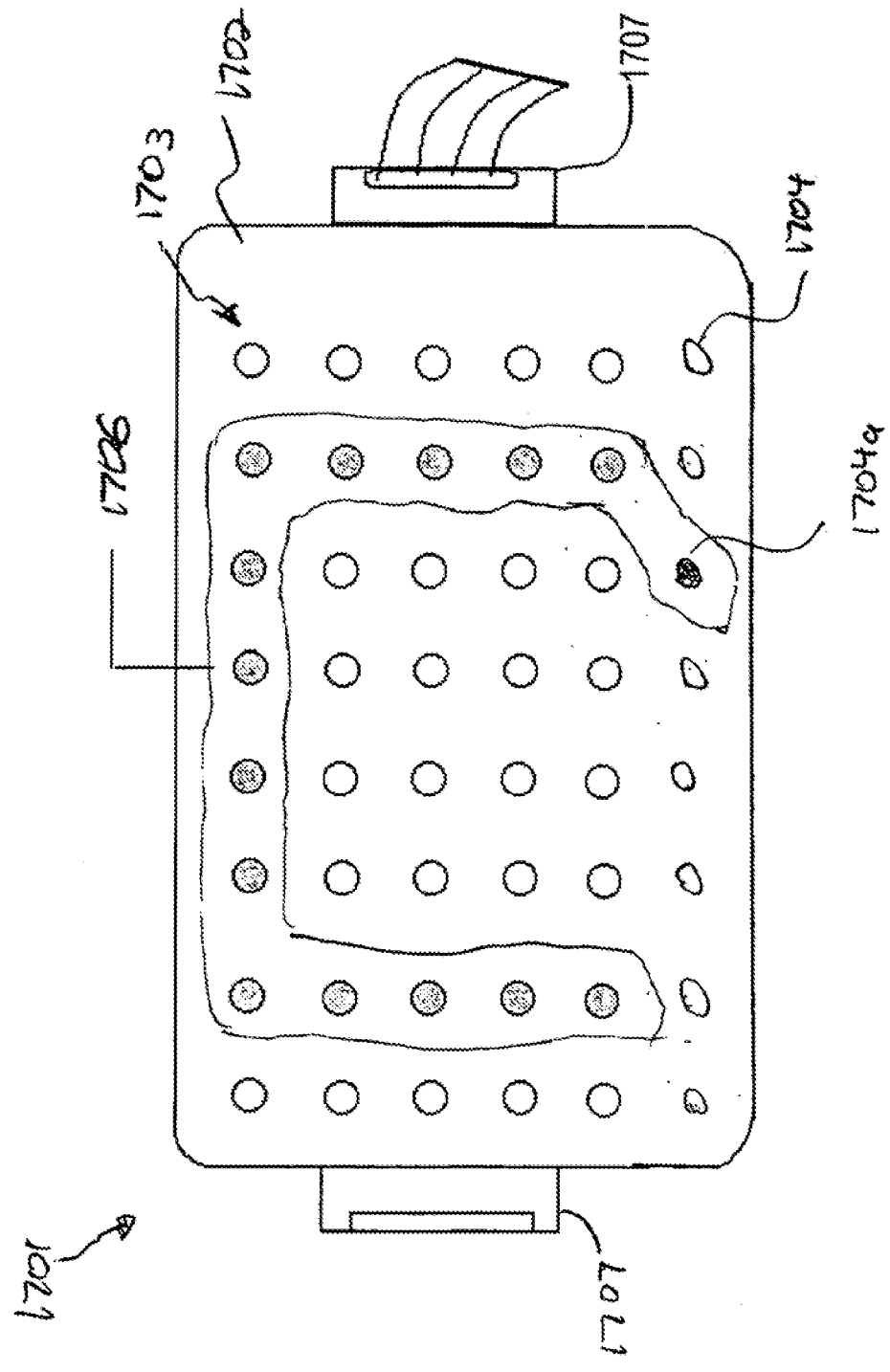
FIG. 17 is a schematic plan view of another embodiment of an apparatus having an array of external electrodes on a support structure for recording signals from the colon and rectum.

In one embodiment of the apparatus of the invention, illustrated in FIG. 17, an apparatus 1701 for diagnosing disorders of a gastrointestinal tract of a mammalian body is provided. More specifically, the apparatus 1701 includes a suitable support structure 1702 such as a flexible sheet of any suitable materials such as one or more layers of plastic, having a sufficient size and shape to overlie the portion of the gastrointestinal tract desired to be monitored. Sheet 1702 can be substantially rectangular in shape and have a suitable size for overlying the colon and rectum, or some lesser combination thereof, of the patient. As can appreciated, the size and shape of the sheet 1702 can be scaled to the size of the patient. An array or grid 1703 of electrodes or sensors 1704 are carried on the support structure. In one embodiment, the size of the array 1703 is suitably sized and the number of electrodes 1704 suitable in number to cover at least the segment of the gastrointestinal tract to be monitored, for example the colon and rectum. The array 1703 can consist of columns and rows of electrodes 1704. A suitable indicia, such as a drawing 1706, resembling the colon and rectum can be provided on the support structure 1702. The indicia 1706 encompasses a portion or set 1704a of the array of electrodes 1704, such set generally having the shape of the colon and rectum. In this manner, only the desired electrodes 1704 are utilized during the monitoring or other procedure, in this example the electrodes 1704 within the drawing 1706 or otherwise noted by the indicia. Similar apparatus can provided from the sheet 1702 with other drawings or other indicia thereon resembling other organs or portions of the gastrointestinal tract, or other sized colons and rectums, provided thereon, and thus a single array 1703 of electrodes can be utilized for multiple applications, and a single sheet of electrodes 1704 arranged in columns and rows or other suitable configurations cut and sized for one or more applications.

As discussed above with respect to array 1604, portion 1704a of electrodes 1704 can be of any suitable configuration of electrodes 1704. For example one or more electrodes 1704 can be provided at each location along the length of the colon, and the electrodes can be spaced along the length of the colon or other organ at any suitable distance between adjoining electrodes 1704. As discussed above with respect to apparatus 1601, one or more suitable securing means can be provided for securing the sheet 1702 to the desired portion of the body of the patient. In FIG. 17, a securing means in the form of a belt 1707 is shown.

At least one of the plurality of electrodes 1704 may include an accelerometer (not shown) for detecting motion of the patient. The electrodes 1704*a* and any accelerometer are electrically coupled by any suitable means, such as by wires, cables or wireless transmitters and receivers, to a suitable electronic apparatus or device, such as portable electronic device, for recording, and optionally analyzing and displaying, the electrical signals from the colon and rectum detected by the electrodes 1704*a*.

In one embodiment of an apparatus for use in diagnosis or treating disorders of the gastrointestinal tract of a mammalian body such as a person, illustrated in FIG. 18, an apparatus 1801 is provided that can include a support structure 1802 for placement on the skin of the body overlying any suitable segment of the gastrointestinal tract, for example the esophagus and stomach and duodenum. The support structure can be made from any suitable material, and in one embodiment is made of a flexible sheet which can be formed from one or more layers of plastic. A plurality of electrodes or sensors 1803 are carried on the support structure 1802 and positioned relative to each other on the support structure in a suitable array 1804 so as to follow the shape of the esophagus, stomach and duodenum. A suitable esophagus 1806, stomach 1807 and duodenum 1808 are shown in dashed lines in FIG. 18. In the illustrated embodiment, electrodes 1803 are provided on the sheet 1802 for registering or overlying the suitable esophagus 1806, stomach 1807 and duodenum 1808. Although the illustrated array 1804 is shown having sets of three electrodes 1803 spaced along the length of the esophagus, stomach and duodenum, other configurations or electrodes 1803 can be provided in the array 1804. For example, the array 1804 can include only one electrode, or two electrodes 1803, at each location on the esophagus, stomach and duodenum, and thus the array can consist of a plurality of single electrodes spaced apart along the length of the esophagus, stomach and duodenum. Other electrode arrays can be provided for registering with less than all of the esophagus, stomach and duodenum, for example one such other electrode array can include only the esophagus, another such electrode array can include only the esophageal sphincter 1809 and the stomach and duodenum and a further such electrode array can include only the esophagus and the stomach.

The array 1804 of electrodes 1803 are thus being capable of recording electrical signals from the esophagus, stomach and duodenum, or any portion or combination thereof, when the apparatus 1801 is placed on the skin of the patient so that the array 1804 is registered with the desired portions of the esophagus, stomach and/or duodenum, over an extended period of time.

In apparatus 1801, the support structure 1802 may include a securing structure such as a belt 1811 for attaching the apparatus to the patient. Other securing structures such as velcro strips (not shown) can extend from the structure 1802 of securing the apparatus to the patient. The support structure 1802 may include an adhesive (not shown) over all or a portion of the underside of the sheet 1802 for securing the support structure to the skin of the body. At least one of the plurality of electrodes 1803 may include an accelerometer (not shown) for detecting motion of the patient. The electrodes 1803 and any accelerometer are electrically coupled by any suitable means, such as by wires, cables or wireless transmitters and receivers, to a suitable electronic apparatus or device, such as portable electronic device, for recording, and optionally analyzing and displaying, the electrical signals from the colon and rectum detected by the electrodes 1803.

Figure 19:
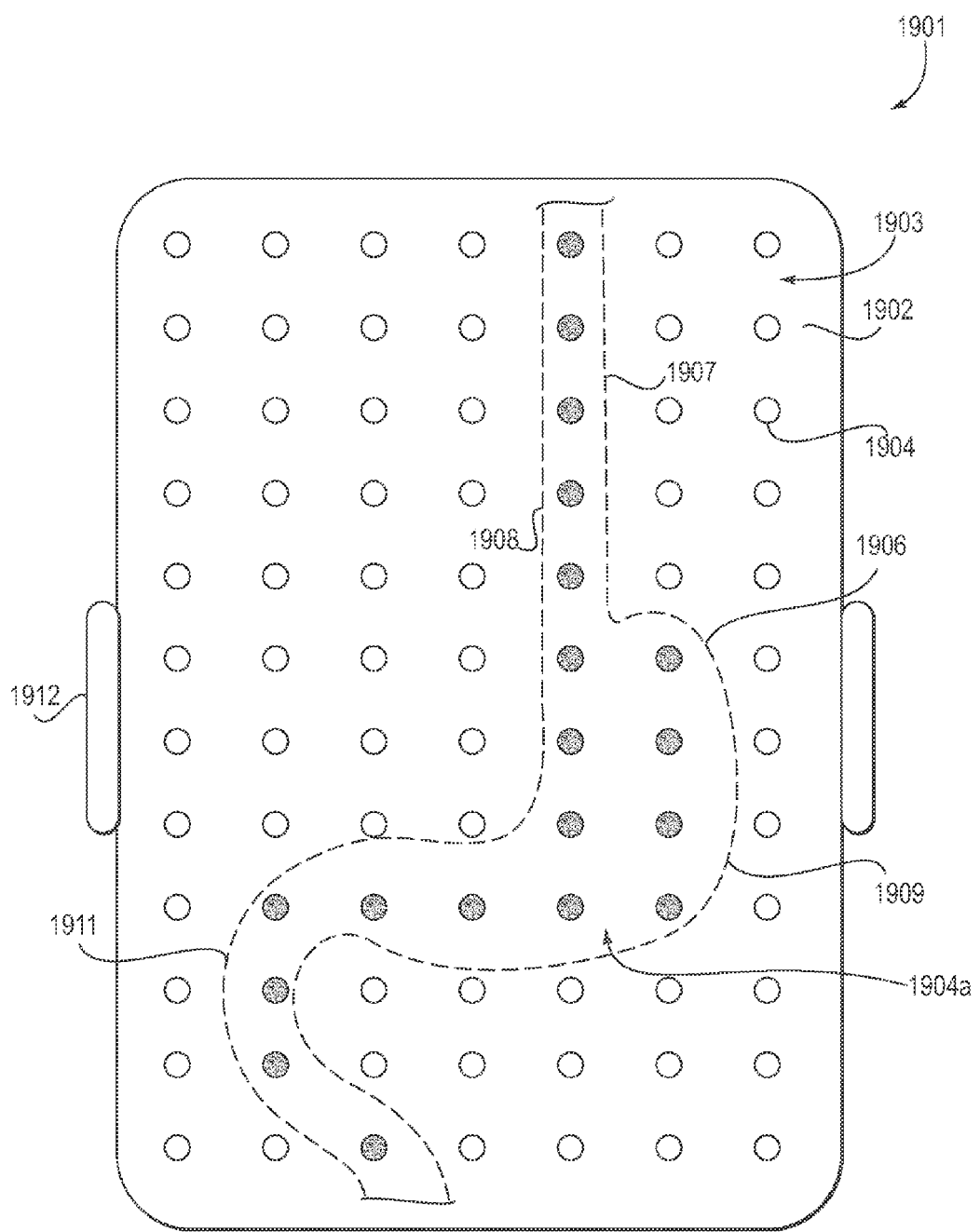
FIG. 19 is a schematic plan view of another embodiment of an apparatus having an array of external electrodes on a support structure for recording signals from the esophagus, stomach and duodenum.

In one embodiment of the apparatus of the invention, illustrated in FIG. 19, an apparatus 1901 for diagnosing disorders of a gastrointestinal tract of a mammalian body is provided. More specifically, the apparatus 1901 includes a suitable support structure 1902 such as a flexible sheet of any suitable materials such as one or more layers of plastic, having a sufficient size and shape to overlie the portion of the gastrointestinal tract desired to be monitored. Sheet 1902 can be substantially rectangular in shape and have a suitable size for overlying the esophagus, stomach and duodenum, or some lesser combination thereof, of the patient. As can appreciated, the size and shape of the sheet 1902 can be scaled to the size of the patient. An array or grid 1903 of electrodes or sensors 1904 are carried on the support structure. In one embodiment, the size of the array 1903 is suitably sized and the number of electrodes 1904 suitable in number to cover at least the segment of the gastrointestinal tract to be monitored, for example the colon and rectum. The array 1903 can consist of columns and rows of electrodes 1904. A suitable indicia, such as a drawing 1906, resembling the esophagus, stomach and duodenum can be provided on the support structure 1902. An esophagus 1907, the esophageal sphincter 1908, the stomach 1909 and the duodenum 1911 are identified on the indicia 1906. The indicia 1906 encompasses a portion or set 1904*a* of the array of electrodes 1904, such set generally having the shape of the esophagus 1907, stomach 1909 and duodenum 1911. In this manner, only the desired electrodes 1904 are utilized during the monitoring or other procedure, in this example the electrodes 1904 within the drawing 1906 or otherwise noted by the indicia. Similar apparatus can provided from the sheet 1902 with other drawings or other indicia thereon resembling other organs or portions of the gastrointestinal tract, or other sized esophagus, stomachs and duodenums, provided thereon, and thus a single array 1903 of electrodes can be utilized for multiple applications, and a single sheet of electrodes 1904 arranged in columns and rows or other suitable configurations cut and sized for one or more applications. For example, indicia 1906 and related portions 1904*a* of electrodes 1904 can be provided for registering with less than all of the esophagus 1907, stomach 1909 and duodenum 1911, for example one such other indicia can include only the esophagus 1907, another such indicia can include only the esophageal sphincter 1908 and the stomach 1909 and duodenum 1911 and a further such indicia can include only the esophagus 1907 and the stomach 1909.

As discussed above with respect to array 1804, portion 1904*a* of electrodes 1904 can be of any suitable configuration of electrodes 1904. For example one or more electrodes 1904 can be provided at each location along the length of the esophagus, stomach and duodenum, and the electrodes can be spaced along the length of the esophagus, stomach and duodenum, or other organ, at any suitable distance between adjoining electrodes 1904. As discussed above with respect to apparatus 1801, one or more suitable securing means can be provided for securing the sheet 1902 to the desired portion of the body of the patient. In FIG. 19, a securing means in the form of a belt 1912 is shown.

At least one of the plurality of electrodes 1904 may include an accelerometer (not shown) for detecting motion of the patient. The electrodes 1904a and any accelerometer are electrically coupled by any suitable means, such as by wires, cables or wireless transmitters and receivers, to a suitable electronic apparatus or device, such as portable electronic device, for recording, and optionally analyzing and displaying, the electrical signals from the colon and rectum detected by the electrodes 1904a.

Figure 20:
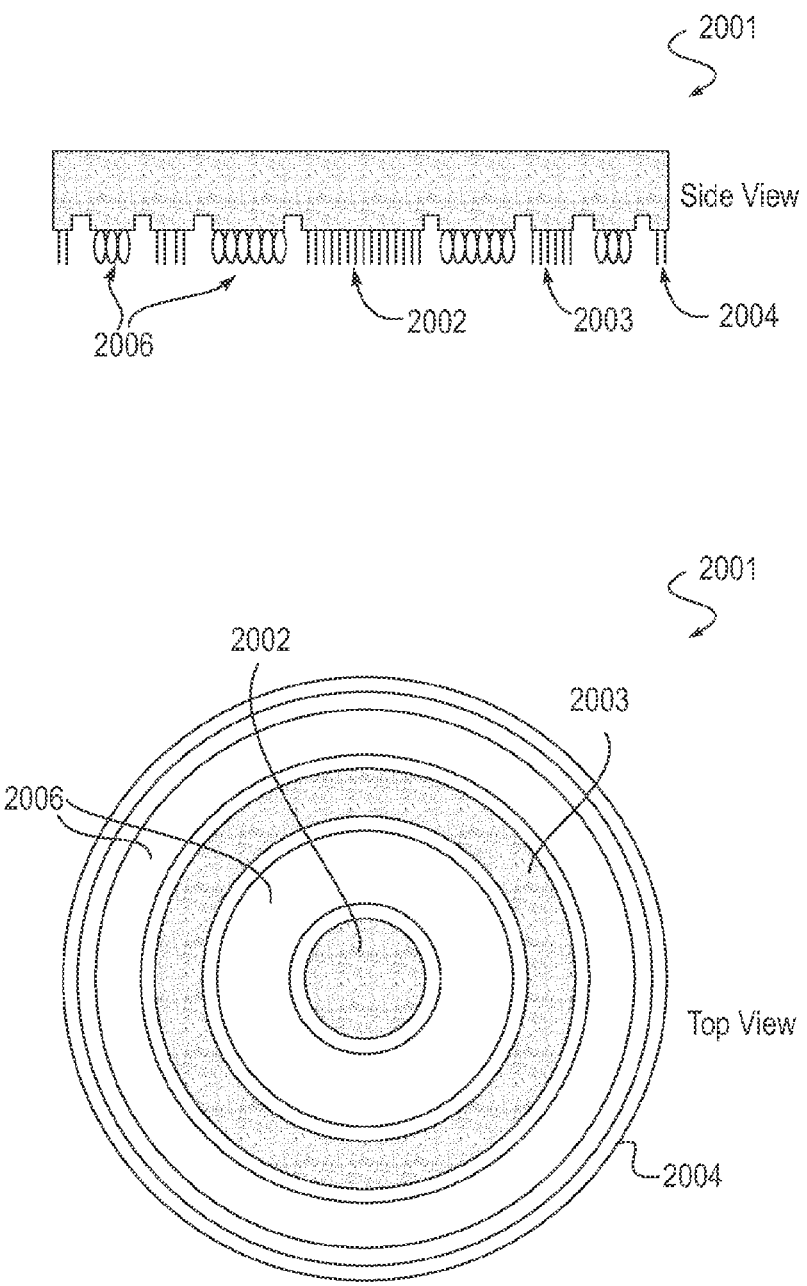
FIG. 20 is a schematic illustration of a sensor of the present invention.

In one embodiment illustrated in FIG. 20, each of the one or more sensors 102 . . . N or electrodes discussed above may be a dry electrode 2001 having three ring electrodes, for example a first or center electrode 2002, a second or intermediate ring electrode 2003 and a third or outer ring electrode 2004, along with amplifier (not shown) and a signal condition unit (not shown) to minimize the noise. The ring electrodes may each have a brush like surface made of a biocompatible highly conductive metal and can acquire signals from the abdominal, chest or other skin surface without interference from hair. The particular arrangement would avoid the need to prep the skin by shaving repeatedly to maintain the long term contact with the skin. The innermost electrode 2002 and outermost ring electrode 2004 may be connected to each other. A bipolar recording may be obtained by filtering out signals common to the middle electrode 2003 and the combination of the inner electrode 2002 and outer electrode 2004, while amplifying the difference. This particular method based on laplacian principle serves to attenuate tangential signals such as cardiac and respiration when recording electrical activity of the gastrointestinal tract, or any portion or segment thereof, from the abdominal surface. As the three ring electrode 2001 is a dry electrode sweat and oils from the skin can interfere with proper signal acquisition. Absorbent surface pads 2006 positioned between the ring electrodes 2002, 2003 and 2004 serve to absorb the sweat and oil from the surface of the skin thus enabling clean recording of the electrical activity. It should be noted that the brush like configuration can be used with monopolar electrodes as well.

In one embodiment, a sensor 102 . . . N of the present invention may be an internal sensor 2101, as illustrated in FIG. 21, and may be swallowed orally or positioned in other parts of the gastrointestinal tract by means of an endoscope. The sensor 2101 can be administered orally, and contains various means to be secured to or detach from the internal lining of gastrointestinal tract, such as for example suction cups, clamps, hooks and an expandable scaffold, that can be deployed wirelessly. A hook 2102 is included on sensor 2101 and shown in FIG. 21. These securing mechanisms 2102 can be made of a biodegradable material to allow the sensor to be detached after a stipulated time so as to allow the sensor to travel down the gastrointestinal tract and be voided. The sensor 2102 may also be equipped with suitable electrical stimulation capability, for example a vibration module 2103, that can enable the sensor to mechanically stimulate the GI tract wirelessly. The sensor 2101, which can include one or more electrodes and is shown having first and second spaced-apart electrodes 2014, may aid in stimulating the gastrointestinal tract to help treat constipation and be used as a tool in biofeedback training.

In another embodiment, the device may be used in pet animals (e.g., cat, dog, rabbit and the like) for the diagnosis and treatment of gastrointestinal or urinary bladder related disease conditions. In another embodiment, in large farm animals (e.g., cattle, buffaloes, sheep, goat, pigs, horses, and the like) a part of the device along with sensors may be placed either outside of the body or inside the gastrointestinal tract of the animals or implanted at other locations in the body to facilitate monitoring of electrical activity of the GI tract.

In one embodiment, a method for diagnosing motility disorders of a gastrointestinal tract of a body of a patient having a gastrointestinal tract is provided and includes measuring electrical signals from the gastrointestinal tract while the patient is engaged in normal daily activities, recording the measured electrical signals on a portable electronic device carried by the body, recording by the patient in real time one or more symptoms of the body selected from the group consisting of bowel movements, cramping, bloating, vomiting, nausea, heartburn, pain from chest, abdomen or pelvic regions, refluxing, incontinence, constipation, stool form, symptoms relating to gastrointestinal disorders including esophageal motility disorders, gastroparesis, gastroesophageal reflux disease, irritable bowel syndrome, constipation, incontinence and dyspepsia, symptoms relating to psychological disorders including stress, depression and anxiety on the portable electronic device during the monitoring step, and analyzing characteristics of the recorded electrical signals with the recorded symptoms of the body to diagnosis gastrointestinal disorders of the body.

Motility disorders of the gastrointestinal tract that can be diagnosed include esophageal motility disorders, motility disorders of the stomach, small and large intestines including gastroparesis, dyspepsia, nausea and vomiting, irritable bowel syndrome, constipation and generalized symptoms such as abdominal pain, cramping and bloating.

In such method, the portable electronic device may be a mobile communications device, and the mobile communications device may be a smart phone. The portable electronic device can have a size and shape for being carried on the body. The portable electronic device can be a hand held electronic device. The step of recording the symptoms of the body may include recording the symptoms on an additional portable electronic device carried by the body. Such method may further include the step of wirelessly transmitting information stored in the portable electronic device to a remote monitoring center. The monitoring step may include monitoring electrical signals when the patient is outside of a hospital and clinical setting. The monitoring step may include monitoring electrical signals when the patient is at home. The monitoring step may include monitoring electrical signals while the patient is ambulatory. Such method may further include measuring electrical signals from the head of the body by means of electroencephalography and the recording the measured electrical signals step may include recording the measured electrical signals from the head of the body on the portable electronic device. Such method may further include measuring electrical signals from skeletal muscles in the abdomen and pelvic regions of the body by means of electromyography and the recording the measured electrical signals step may include recording the measured electrical signals from the skeletal muscles on the portable electronic device. Such method may further include measuring the conductance of the skin of the body and recording the conductance measurements on the portable electronic device, and the analyzing step may include analyzing the recorded conductance measurements with the recorded electrical signals and recorded symptoms of the body to diagnosis gastrointestinal disorders of the body. The monitoring step may include monitoring cardiac electrical signals by means of electrocardiography and the recording the measured electrical signals step may include recording cardiac electrical signals on the portable electronic device.

Such method may further include measuring respiratory signals while the patient is engaged in normal daily activities and the recording the measured electrical signals step may include recording the measured respiratory signals on the portable electronic device. The characteristics of the recorded electrical signals may be selected from the group consisting of frequency, amplitude, power and periodicity. Such method may further include measuring the motion of the body, and the analyzing step may include analyzing characteristics of the recorded electrical signals with the motion of the body and the recorded symptoms of the body to diagnosis gastrointestinal disorders of the body. Such method may further include recording events of the body selected from the group consisting of eating, drinking, bowel movement, emesis, walking, jogging, traveling in a vehicle and sitting, and wherein the analyzing step includes analyzing characteristics of the recorded electrical signals with the recorded events of the body and the recorded symptoms of the body to diagnosis gastrointestinal disorders of the body.

In one embodiment, a method for diagnosing motility disorders of a gastrointestinal tract of a body of a patient having a gastrointestinal tract is provided and includes placing a plurality of electrodes on the skin of the body at least in the vicinity of the gastrointestinal tract, monitoring electrical signals from the gastrointestinal tract from the plurality of electrodes while the patient is engaged in normal daily activities, recording the electrical signals on a portable electronic device carried by the body, recording one or more symptoms of the body selected from the group consisting of bowel movements, cramping, bloating, vomiting, nausea, heartburn, pain from chest, abdomen or pelvic regions, refluxing, incontinence, constipation, stool form, symptoms relating to gastrointestinal disorders including esophageal motility disorders, gastroparesis, gastroesophageal reflux disease, irritable bowel syndrome, constipation, incontinence and dyspepsia, symptoms relating to psychological disorders including stress, depression and anxiety on the portable electronic device during the monitoring step, and analyzing characteristics of the recorded electrical signals with the recorded symptoms of the body to diagnosis gastrointestinal disorders of the body.

In such method, the plurality of electrodes may be wired to the portable electronic device. The plurality of electrodes wirelessly may communicate with the portable electronic device. The placing step may include placing at least one electrode in the gastrointestinal tract of the body, and the monitoring step may include monitoring electrical signals from the at least one electrode in the gastrointestinal tract of the body and the recording the electrical signals step includes recording electrical signals from the at least one electrode in the gastrointestinal tract on the portable electronic device. The placing step may include placing a plurality of additional electrodes on the head of the body, and the monitoring step may include monitoring electrical signals from the plurality of additional electrodes by means of electroencephalography and the recording the electrical signals step includes recording electrical signals from the plurality of additional electrodes on the portable electronic device. The placing step may include placing a plurality of additional electrodes on the abdomen and pelvic regions of the body, and the monitoring step may include monitoring electrical signals from skeletal muscles by means of the plurality of additional electrodes and electromyography and the recording the electrical signals step may include recording electrical signals from the plurality of additional electrodes on the portable electronic device. Such method may further include measuring the conductance of the skin of the body and recording the conductance measurements on the portable electronic device, and the analyzing step may include analyzing the recorded conductance measurements with the recorded electrical signals and recorded symptoms of the body to diagnosis gastrointestinal disorders of the body. The monitoring step may include monitoring cardiac electrical signals from the plurality of electrodes by means of electrocardiography and the recording the electrical signals step may include recording cardiac electrical signals on the portable electronic device. Such method may further include placing a plurality of sensors on the exterior of the body at least in the vicinity of the chest and obtaining respiratory signals from the plurality of sensors while the patient is engaged in normal daily activities so as to provide corresponding electrical signals by the plurality of sensors, and the recording the electrical signals step may include recording corresponding electrical signals from the plurality of sensors on the portable electronic device. Such method may further include mounting an accelerometer on the body for monitoring motion of the body, and the analyzing step may include analyzing characteristics of the recorded electrical signals with the motion of the body and the recorded symptoms of the body to diagnosis gastrointestinal disorders of the body. The at least one of the plurality of electrodes may include an accelerometer for monitoring motion of the body and the analyzing step may include analyzing characteristics of the recorded electrical signals with the motion of the body and the recorded symptoms of the body to diagnosis gastrointestinal disorders of the body. The placing step may include placing the plurality of electrodes on the exterior of the body at least in the vicinity of the esophagus, stomach and large and small intestines.

In one embodiment, a method for treating constipation of a person having a gastrointestinal tract including a colon and a rectum and abdominal and pelvic floor muscles is provided and includes measuring electrical signals from the gastrointestinal tract, measuring additional electrical signals from the abdominal and pelvic floor muscles, displaying the electrical signals and the additional electrical signals on an electronic apparatus, having the person sensing content in the colon and rectum by focusing sensations selected from the group consisting of pressure, pain and sounds of the abdominal and pelvic regions, observing an increase in the electrical signals to confirm contraction of the colon and rectum and thus the existence of the content in the colon and rectum, refraining from excessively contracting the abdominal and pelvic floor muscles until the content reaches the rectum, observing the additional electrical signals during the refraining step to confirm minimal contraction of the abdominal and pelvic floor muscles until the content reaches the rectum and contracting the abdominal and pelvic floor muscles once the content reaches the rectum to void the contents from the gastrointestinal tract.

Such method may further include viewing an increase in the additional electrical signals during the contracting step to confirm contraction of the abdominal and pelvic floor muscles. Such method may further include acquiring electroencephalographic signals from the head of the person, displaying the electroencephalographic signals on the electronic apparatus, and viewing the electroencephalographic signals during the having step to confirm that the central nervous system is in a relaxed state so as to facilitate contraction of the colon.

In one embodiment, a method for treating constipation of a person having a gastrointestinal tract including a colon and a rectum and abdominal and pelvic floor muscles is provided and includes mounting a plurality of electrodes on the skin of the person at least in the vicinity of the colon and rectum, mounting at least one additional electrode in the vicinity of the abdominal and pelvic floor muscles, coupling the plurality of electrodes and the at least one electrode to an electronic apparatus, having the person prepare for a bowel movement, acquiring electrical signals from the gastrointestinal tract by means of the plurality of electrodes and electrical signals from the abdominal and pelvic floor muscles from the at least one additional electrode and displaying such electrical signals on the electronic apparatus, having the person sensing content in the colon and rectum by focusing sensations selected from the group consisting of pressure, pain and sounds of the abdominal and pelvic regions, observing an increase in the electrical signals from the plurality of electrodes to confirm contraction of the colon and rectum and thus the existence of the content in the colon and rectum, refraining from excessively contracting the abdominal and pelvic floor muscles until the content reaches the rectum, observing the electrical signal from the at least one additional electrode during the refraining step to confirm minimal contraction of the abdominal and pelvic floor muscles until the content reaches the rectum and contracting the abdominal and pelvic floor muscles once the content reaches the rectum to void the contents from the gastrointestinal tract.

In one embodiment, an apparatus for diagnosing disorders of a gastrointestinal tract of a mammalian body having a gastrointestinal tract that includes an esophagus and stomach and a colon and rectum is provided and includes a support structure for placement on the skin of the body overlying a segment of the gastrointestinal tract selected from the group consisting of the esophagus and stomach and the colon and rectum, a plurality of electrodes carried on the support structure and being positioned relative to each other on the support structure so as to follow the shape of the selected esophagus and stomach or the colon and rectum and thus being capable of recording electrical signals from the selected esophagus and stomach or the colon and rectum over an extended period of time when the support structure is placed on the skin of the body.

In such apparatus, the support structure may include a belt. The support structure may include a flexible sheet of plastic. The support structure may include an adhesive for securing the support structure to the skin of the body. The at least one of the plurality of electrodes may include an accelerometer. The electronic device may be a portable electronic device having a size and shape for being carried on the body. The electronic device may be a hand held electronic device.

In one embodiment, an apparatus for diagnosing disorders of a gastrointestinal tract of a mammalian body having a gastrointestinal tract that includes an esophagus and stomach and a colon and rectum is provided and includes a support structure for placement on the skin of the body overlying a portion of the gastrointestinal tract, an array of electrodes carried on the support structure and having a size at least as large as a segment of the gastrointestinal tract selected from the group consisting of the esophagus and stomach and the colon and rectum, an indicia resembling the selected esophagus and stomach or the colon and rectum provided on the support structure and encompassing a portion of the array of electrodes having a shape of the selected esophagus and stomach or the colon and rectum and thus capable of recording electrical signals from the selected esophagus and stomach or the colon and rectum over an extended period of time when the support structure is placed on the skin of the body.

In such apparatus, the support structure may include a belt. The support structure may include a flexible sheet of plastic. The support structure may include an adhesive for securing the support structure to the skin of the body. The at least one of the plurality of electrodes may include an accelerometer. The electronic device may include a portable electronic device having a size and shape for being carried on the body. The electronic device may include a hand held electronic device.

In one embodiment, a method for treating urinary incontinence of a person having a urinary bladder is provided and includes mounting a plurality of electrodes on the exterior of the person at least in the vicinity of the urinary bladder, coupling the plurality of electrodes to an electronic apparatus, acquiring electrical signals from the urinary bladder by means of the plurality of electrodes and displaying such electrical signals on the electronic apparatus, observing an increase in the electrical signals from the plurality of electrodes to monitor contraction of the urinary bladder, distracting the person's attention away from the bladder and observing a decrease in the electrical signals on the electronic apparatus confirming relaxation of the urinary bladder.

In such method, the step of observing an increase in the electrical signals may include viewing the electronic signals on the electronic apparatus. The step of observing an increase in the electrical signals may include an alarm provided in the electronic apparatus. Such method may further include notifying the person of contractions of the urinary bladder associated with potential leakage. Such method may further include acquiring electroencephalographic signals from the head of the person associated with the urge to urinate, displaying the electroencephalographic signals on the electronic apparatus, and after commencement of the distracting step viewing the electroencephalographic signals to confirm that the central nervous system is in a relaxed state which leads to reduction in the contractions of the urinary bladder.

In one embodiment, a method for treating bloating of a person having a gastrointestinal tract including a stomach and abdominal muscles is provided and includes mounting a first plurality of electrodes on the skin of the person in the vicinity of the stomach, mounting a second plurality of electrodes on the skin of the person in the vicinity of the abdominal muscles, mounting a third plurality of electrodes on the head of the person, coupling the first, second and third plurality of electrodes to an electronic apparatus, acquiring electrical signals from the stomach by means of the first plurality of electrodes and electromyographic signals from the abdominal muscles from the second plurality of electrodes and electroencephalographic signals from the head by the third plurality of electrodes and displaying such signals on the electronic apparatus, monitoring the electroencephalographic signals for an increase in stress when the person is experiencing symptoms of bloating, observing any increase in the electromyographic signals associated with increase in activity of the abdominal muscles, observing any change in the electrical signals from the stomach and, if a significant increase in the electroencephalographic signals associated with stress and the electromyographic signals and no significant change in the electrical signals, having the person relax so as to cause the symptoms of bloating to decrease.

Such method may further include measuring the conductance of the skin of the body and recording the conductance measurements on the electronic apparatus, observing any increase in the skin conductance and, if an increase in the electroencephalographic signals associated with stress and the electromyographic signal and in the skin conductance and no significant change in the electrical signals, having the person relax.

In one embodiment, a method for treating irritable bowel syndrome of a person having a gastrointestinal tract including a stomach and abdominal muscles is provided and includes mounting a first plurality of electrodes on the skin of the person in the vicinity of the small and large intestines, mounting a second plurality of electrodes on the head of the person, coupling the first and second plurality of electrodes to an electronic apparatus, acquiring electrical signals from the small and large intestines by means of the first plurality of electrodes and electroencephalographic signals from the head by the second plurality of electrodes and displaying such signals on the electronic apparatus, monitoring the electroencephalographic signals for an increase in stress when the person is experiencing symptoms of irritable bowel syndrome, observing any increase in the electroencephalographic signals associated with stress and the electrical signals associated with increased frequency of bowel movements and having the person relax if a change in electrical signals are noted that correlate with changes in bowel habits.

Such method may further include measuring the conductance of the skin of the body and recording the conductance measurements on the electronic apparatus, observing any increase in the skin conductance and, if an increase in the electroencephalographic signals associated with stress and the electrical signals associated with increased frequency of bowel movements and in the skin conductance, having the person relax.

In one embodiment, a method for monitoring a gastrointestinal tract of an animal is provided and includes placing a plurality of electrodes on the skin of the animal at least in the vicinity of the gastrointestinal tract, monitoring electrical signals from the gastrointestinal tract from the plurality of electrodes, recording the electrical signals on an electronic apparatus, and comparing characteristics of the recorded electrical signals with comparable characteristics of electrical signals from a healthy animal to detect disruption of gastrointestinal activity.

In such method, the comparing step may include diagnosing displacement of the abomasum in farm animals. The comparing step may include determining the location of the abomasum based on the analysis of frequency, amplitude and direction of the electrical signals from abomasum with respect to other organs and anatomical land marks, and the displacement of the electrical signals away from the normal anatomical location of the abomasum on the lower right side of the abdomen. The comparing step may include detecting abnormal motility patterns of disorders selected from the group consisting of rumen, reticulum, omasum and abomasum in farm animals.

In addition, it will be appreciated that the various examples and methods disclosed herein may be embodied using many different equipments and steps. Accordingly, the specification and figures are to be regarded in an illustrative rather than a restrictive sense.

I claim:

1. A method for facilitating diagnosis of motility disorders of a gastrointestinal tract of a body of a patient, the method performed by a portable electronic device carried by the body and wirelessly connected to a plurality of external electrodes, the method comprising:
   acquiring, by the portable electronic device, electrical signals from the plurality of wirelessly connected external electrodes while the patient is engaged in normal daily activities, wherein the electrical signals include electromyography signals concurrently acquired from a plurality of organs of the gastrointestinal tract, wherein the organs include a stomach, small intestines, and large intestines, wherein each of the organs produces a separate electromyography signal, and wherein the electrical signals are acquired from external electrodes positioned in a circular pattern on the skin of the body over the patient's abdomen;
   recording the acquired electrical signals to memory on the portable electronic device;
   processing, by a processor of the portable electronic device, the acquired electrical signals to generate a plurality of processed waveforms;
   recording, to memory on the portable electronic device, one or more inputs entered by the patient for one or more symptoms of the body selected from a group consisting of: bowel movements, cramping, bloating, vomiting, nausea, heartburn, pain from chest, abdomen, or pelvic regions, refluxing, incontinence, constipation, stool form, and symptoms relating to esophageal motility disorders, incontinence, or other gastrointestinal disorder;
   correlating, by the processor, the processed waveforms to the patient-entered symptoms based on time;
   identifying, by the processor, a plurality of characteristics of the processed waveforms, wherein the characteristics of the processed waveforms are selected from a group consisting of: frequency, amplitude, power, pattern, duration, and periodicity;
   identifying, by the processor, the respective organ associated with each processed waveform and the organs that experienced electrical activity during a duration of time, based on the plurality of characteristics of the processed waveforms;
   characterizing, by the processor, the processed waveforms as being indicative of normal or abnormal activity of the organs based on the plurality of characteristics of the processed waveforms; and
   outputting, from the processor to a display, an alert indicative of a status of normal or abnormal activity of the organs.

2. The method of claim 1, further comprising wirelessly transmitting information stored in the portable electronic device to a remote monitoring center.

3. The method of claim 1, further comprising acquiring and recording, by the portable electronic device, electrical signals from sensors on the head of the body by means of electroencephalography.

4. The method of claim 1, further comprising acquiring and recording, by the portable electronic device, electrical signals from sensors placed over skeletal muscles in the abdomen and pelvic regions of the body by means of electromyography.

5. The method of claim 1, further comprising acquiring and recording, by the portable electronic device, conductance of the skin of the body measured by conductance sensors positioned on the skin.

6. The method of claim 1, further comprising acquiring and recording, by the portable electronic device, cardiac electrical signals from sensors positioned on a chest of the body by means of electrocardiography.

7. The method of claim 1, further comprising acquiring and recording, by the portable electronic device, respiratory signals while the patient is engaged in daily activities.

8. The method of claim 1, further comprising acquiring and recording, by the portable electronic device, motion of the body.

9. The method of claim 1, further comprising recording data entered by the patient indicative of one or more events of the body selected from a group consisting of eating, inking, bowel movement, emesis, walking, jogging, traveling in a vehicle, and sitting.

10. The method of claim 1, wherein recording the acquired electrical signals comprises recording sequential propagation of electrical activity from a plurality of segments of the gastrointestinal tract.

11. The method of claim 1, wherein the one or more inputs entered by the patient are recorded with a time stamp.

12. The method of claim 1, wherein the electrical signals are recorded for a period ranging from one minute to seven days.

* * * * *

UNITED STATES PATENT AND TRADEMARK OFFICE
CERTIFICATE OF CORRECTION

PATENT NO. : 9,474,482 B2
APPLICATION NO. : 13/373042
DATED : October 25, 2016
INVENTOR(S) : Udaya Sankar Devanaboyina It is certified that error appears in the above-identified patent and that said Letters Patent is hereby corrected as shown below:

In Claim 9, Column 29, Line 7, "inking" should be changed to -- drinking --

Signed and Sealed this
Twenty-sixth Day of December, 2017

Joseph Matal
*Performing the Functions and Duties of the
Under Secretary of Commerce for Intellectual Property and
Director of the United States Patent and Trademark Office*